(12) United States Patent
Herráiz Sierra et al.

(10) Patent No.: US 11,104,702 B2
(45) Date of Patent: Aug. 31, 2021

(54) PROCESS AND INTERMEDIATES FOR THE SYNTHESIS OF OBETICHOLIC ACID AND DERIVATIVES THEREOF

(71) Applicant: Crystal Pharma, S.A.U., Boecillo-Valladolid (ES)

(72) Inventors: Ignacio Herráiz Sierra, Valladolid (ES); Yolanda Fernández Sainz, Valladolid (ES); Carlos Cordovilla Losada, Valladolid (ES); Alfonso Pérez Encabo, Valladolid (ES); José Angel Turiel Hernandez, Valladolid (ES)

(73) Assignee: CRYSTAL PHARMA, S.A.U., Boecillo-Valladolid (ES)

( * ) Notice: Subject to any disclaimer, the term of this patent is extended or adjusted under 35 U.S.C. 154(b) by 0 days.

(21) Appl. No.: 16/632,304

(22) PCT Filed: Jun. 22, 2018

(86) PCT No.: PCT/EP2018/066778
§ 371 (c)(1),
(2) Date: Jan. 17, 2020

(87) PCT Pub. No.: WO2019/015914
PCT Pub. Date: Jan. 24, 2019

(65) Prior Publication Data
US 2020/0165289 A1    May 28, 2020

(30) Foreign Application Priority Data

Jul. 18, 2017 (EP) .................................. 173824715

(51) Int. Cl.
*C07J 9/00* (2006.01)
*C07J 31/00* (2006.01)
*C07J 71/00* (2006.01)

(52) U.S. Cl.
CPC .............. *C07J 9/005* (2013.01); *C07J 31/006* (2013.01); *C07J 71/001* (2013.01)

(58) Field of Classification Search
CPC ............... C07J 9/00; C07J 31/00; C07J 71/00
See application file for complete search history.

(56) References Cited

FOREIGN PATENT DOCUMENTS

| CN | 105348365 A | 2/2016 |
|----|-------------|--------|
| CN | 105399793 A | 3/2016 |

(Continued)

OTHER PUBLICATIONS

International Search Report With Written Opinion, dated Sep. 6, 2018, in International Application No. PCT/EP2018/066778.

(Continued)

*Primary Examiner* — Brenda L Coleman
(74) *Attorney, Agent, or Firm* — Knobbe, Martens, Olson & Bear LLP

(57) ABSTRACT

A process for the preparation of obeticholic acid and derivatives thereof by:

(a) hydrogenation of the double bond and reductive opening of the epoxide of a compound of formula (II) or a salt or solvate thereof

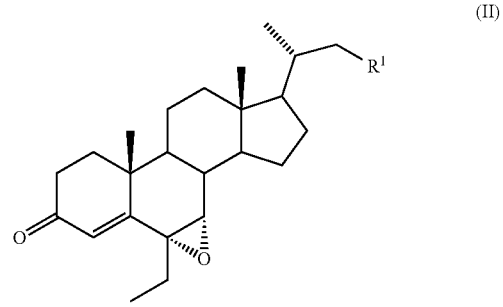

to obtain a compound of formula (IIIa) and/or (IIIb), or salts or solvates thereof

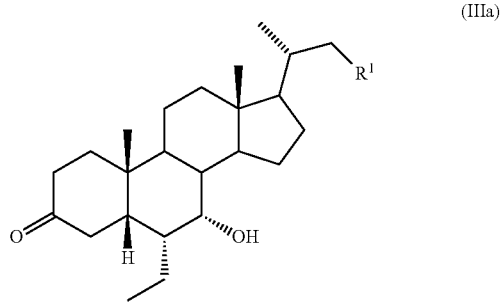

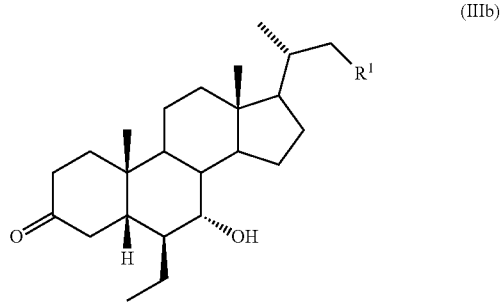

and (b) conversion of a compound of formula (IIIa) and/or a compound of formula (IIIb), or a salt or solvate thereof, into a compound of formula (I), or a salt or solvate thereof (Continued)

(I)

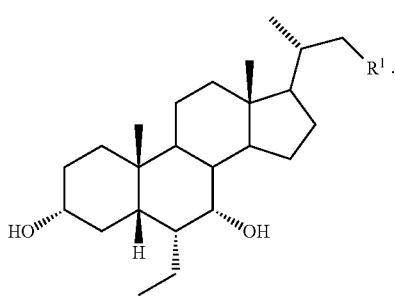

18 Claims, 1 Drawing Sheet

(56) References Cited

FOREIGN PATENT DOCUMENTS

| EP | 0 424 232 B1 | 2/1996 |
|---|---|---|
| EP | 1 392 714 B1 | 8/2005 |
| EP | 1 888 614 B1 | 12/2009 |
| WO | WO 2016/079517 A1 | 5/2016 |
| WO | WO 2016/079518 A1 | 5/2016 |
| WO | WO 2016/079519 A1 | 5/2016 |
| WO | WO 2016/079520 A1 | 5/2016 |
| WO | WO 2016/173397 A1 | 11/2016 |
| WO | WO 2016/173524 A1 | 11/2016 |
| WO | WO-2017199033 A1 * | 11/2017 ........... C07J 41/0094 |
| WO | WO-2017199039 A1 * | 11/2017 .............. C07J 9/005 |

OTHER PUBLICATIONS

International Preliminary Report on Patentability, dated Jan. 21, 2020, in international Application No. PCT/EP2018/066778.

* cited by examiner

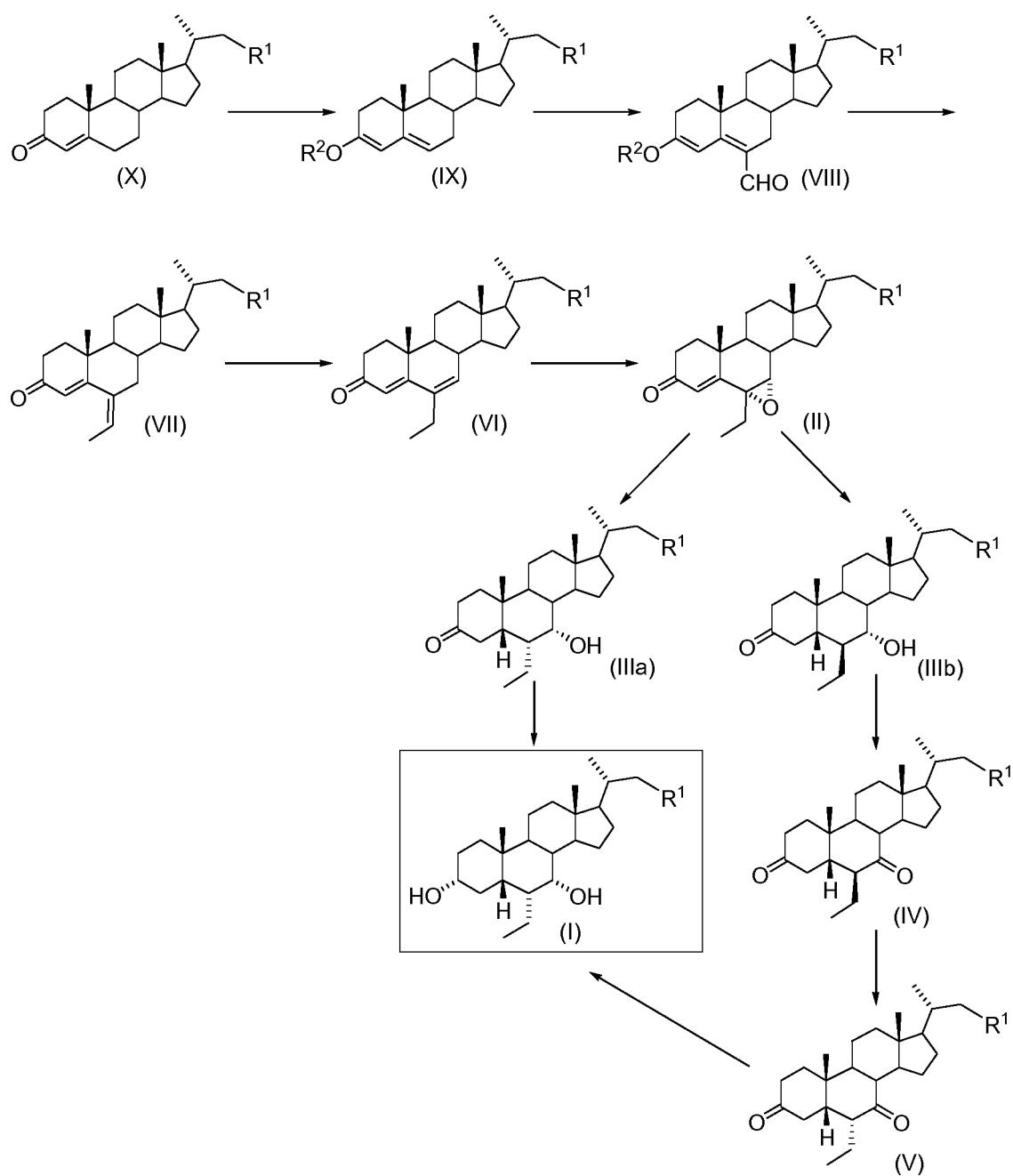

PROCESS AND INTERMEDIATES FOR THE SYNTHESIS OF OBETICHOLIC ACID AND DERIVATIVES THEREOF

PRIORITY AND CROSS REFERENCE TO RELATED APPLICATIONS

This application is the U.S. National Phase Application under 35 U.S.C. § 371 of International Application No. PCT/EP2018/066778, filed Jun. 22, 2018, designating the U.S. and published in English as WO 2019/015914 A1 on Jan. 24, 2019, which claims the benefit of European Application No. EP 17382471.5, filed Jul. 18, 2017. Any and all applications for which a foreign or a domestic priority is claimed is/are identified in the Application Data Sheet filed herewith and is/are hereby incorporated by reference in their entirety under 37 C.F.R. § 1.57.

FIELD OF THE INVENTION

The invention relates to a process for the preparation of obeticholic acid and derivatives thereof and to intermediates useful in the synthesis of these compounds.

BACKGROUND OF THE INVENTION

The present invention relates to a process for the preparation of obeticholic acid and derivatives thereof of potential pharmaceutical value as highly potent FXR-agonist. These compounds can be used for the treatment of liver and gastrointestinal disorders, such as primary biliary cirrhosis (PBC), nonalcoholic steatohepatitis (NASH), portal hypertension, etc.

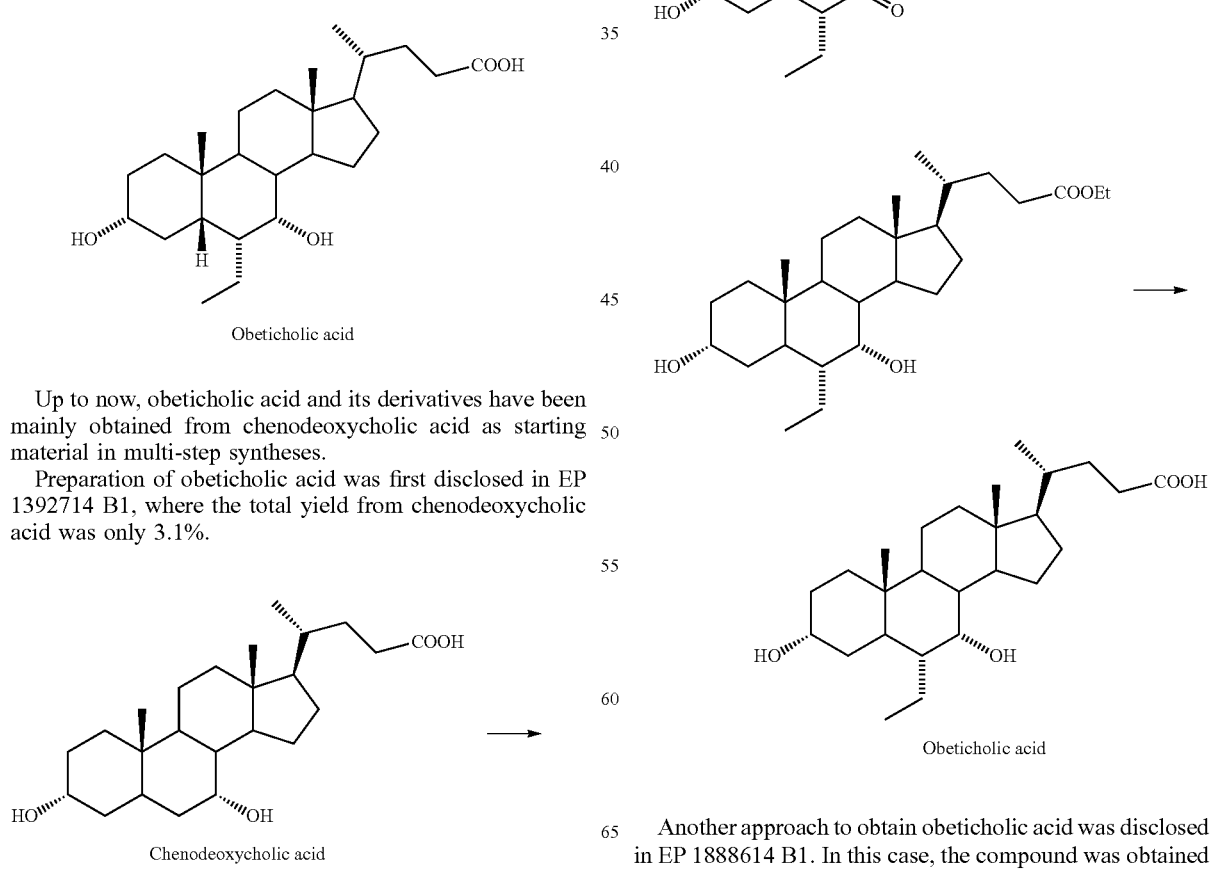

Obeticholic acid

Up to now, obeticholic acid and its derivatives have been mainly obtained from chenodeoxycholic acid as starting material in multi-step syntheses.

Preparation of obeticholic acid was first disclosed in EP 1392714 B1, where the total yield from chenodeoxycholic acid was only 3.1%.

Chenodeoxycholic acid

Obeticholic acid

Another approach to obtain obeticholic acid was disclosed in EP 1888614 B1. In this case, the compound was obtained in 25% total yield after nine synthetic steps.

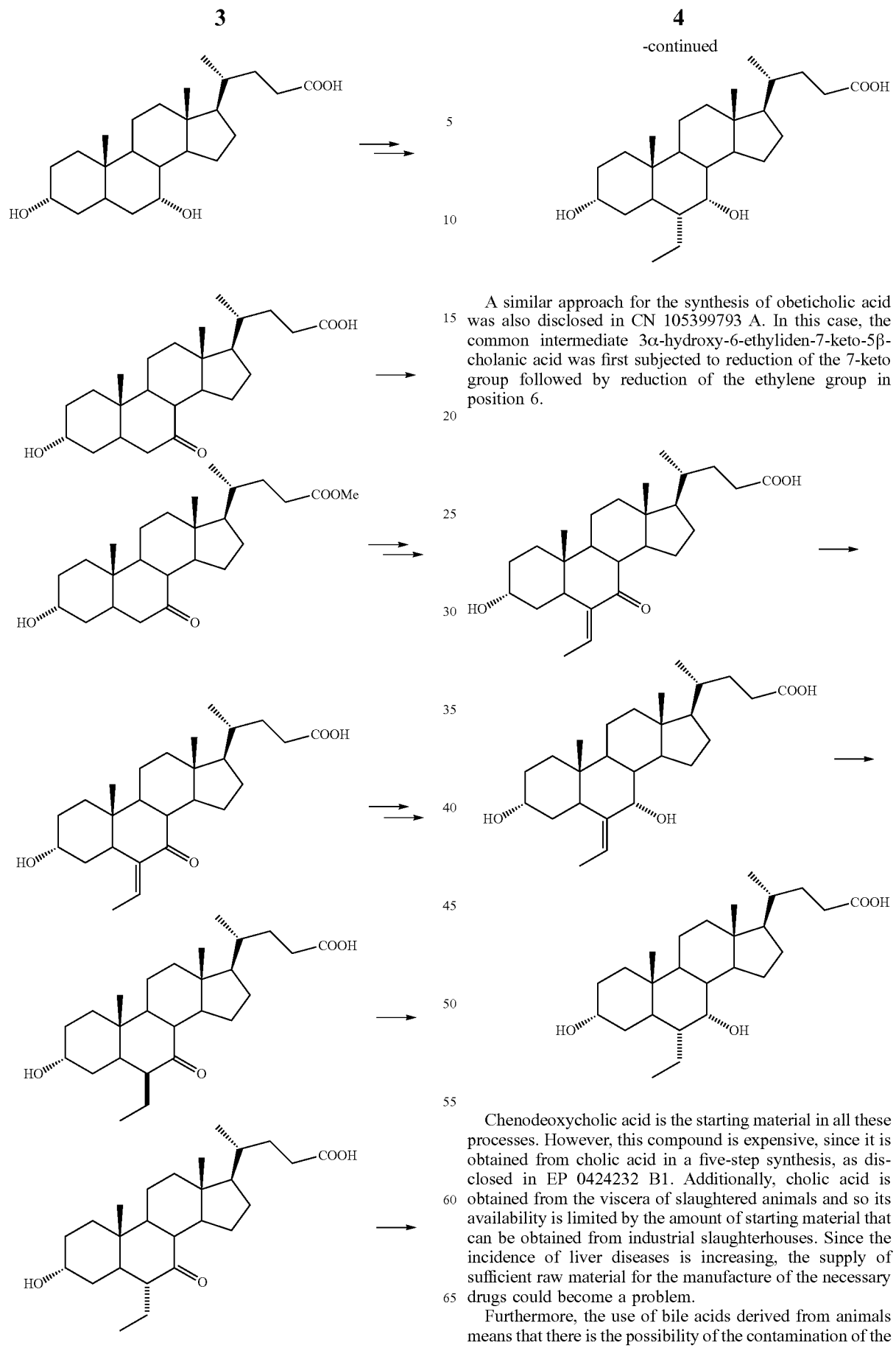

A similar approach for the synthesis of obeticholic acid was also disclosed in CN 105399793 A. In this case, the common intermediate 3α-hydroxy-6-ethyliden-7-keto-5β-cholanic acid was first subjected to reduction of the 7-keto group followed by reduction of the ethylene group in position 6.

Chenodeoxycholic acid is the starting material in all these processes. However, this compound is expensive, since it is obtained from cholic acid in a five-step synthesis, as disclosed in EP 0424232 B1. Additionally, cholic acid is obtained from the viscera of slaughtered animals and so its availability is limited by the amount of starting material that can be obtained from industrial slaughterhouses. Since the incidence of liver diseases is increasing, the supply of sufficient raw material for the manufacture of the necessary drugs could become a problem.

Furthermore, the use of bile acids derived from animals means that there is the possibility of the contamination of the material with infectious agents present in the viscera, such as prions, viruses and other toxins, which could potentially contaminate obeticholic acid and makes it necessary to take more strict controls of the cattle and slaughterhouses and of the synthesis.

For these reasons, and because there are new bile acid derivatives that are more difficult to obtain by the known methods (such as INT-767 or ECDCOH), there is a need for other starting materials different from chenodeoxycholic acid, preferably starting materials of plant origin. These starting materials should provide improved and more versatile syntheses that allow the preparation of obeticholic acid, but also other potentially therapeutic derivatives such as INT-767 or ECDCOH.

Through most of the published processes starts from chenodeoxycholic acid, a series of patents have been recently published: WO 2016/079517, WO 2016/079518, WO 2016/079519 and WO 2016/079520, regarding the synthesis of obeticholic acid from natural sources such as ergosterol or stigmasterol of plant origin or deoxycholic acid of animal origin. In particular, the following process is disclosed in these patent applications:

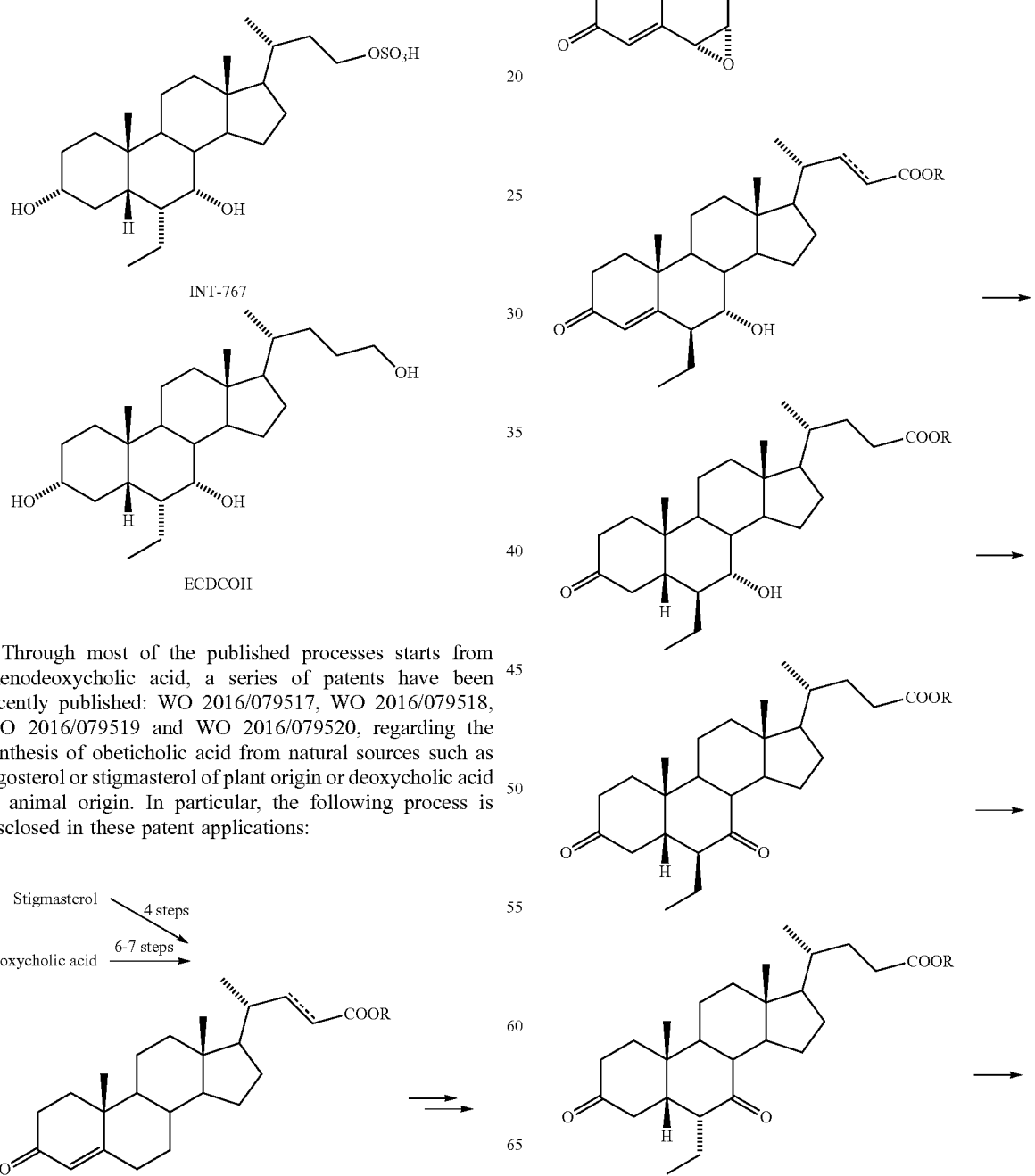

-continued

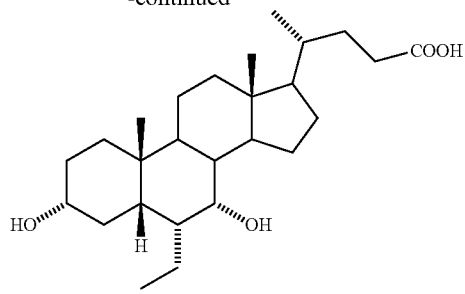

Ergosterol and Stigmasterol are expensive starting materials because a previous process of separation from the rest of phytosterols present in the vegetable oils is necessary. In addition to this initial cost, the above synthesis requires many steps to obtain obeticholic acid. Opening of the epoxy ring gives rise to the 6β,7α-isomer and so additional steps are needed to epimerize the carbon at position 6 in order to obtain obeticholic acid.

It is therefore necessary to develop a new process for obtaining obeticholic acid and derivatives thereof as well as key intermediates in the synthesis of these compounds which overcome all or part of the problems associated with the known processes belonging to the state of the art.

SUMMARY OF THE INVENTION

The invention faces the problem of providing a new process for the preparation of obeticholic acid and derivatives thereof which does not require the use of chenodeoxycholic acid, or other compounds obtained from animal sources, as starting material. In particular, the inventors have found that compounds of formula (II) can be efficiently used as intermediates in the synthesis of obeticholic acid and related compounds. These compounds can be obtained from 3-keto-bisnorcholenol

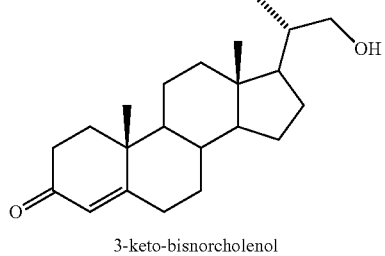

3-keto-bisnorcholenol

3-Keto-bisnorcholenol is a raw material of vegetable origin very suitable for obtaining obeticholic acid and other bile acid derivatives, especially those with modifications in the lateral chain, such as INT-767 or ECDCOH.

3-Keto-bisnorcholenol is obtained by direct fermentation of phytosterols obtained from deodorized vegetable oils, where purification prior to the fermentation stage is not necessary and therefore it constitutes a very cheap raw material Therefore, in a first aspect of the present invention there is provided a compound of formula (II) or a salt or solvate thereof

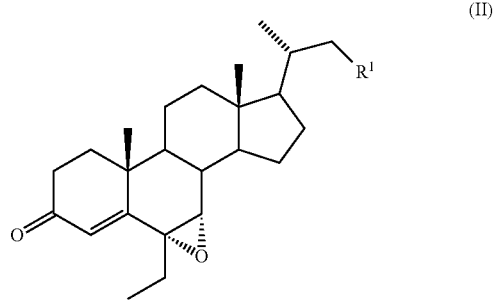

wherein $R^1$ is selected from the group consisting of —(CH$_2$)n-OR, —(CH$_2$)n-COOR, —(CH$_2$)n-CONR$_2$, —(CH$_2$)n-CH(COOR)$_2$, —(CH$_2$)n-CN, —(CH$_2$)n-halogen, —(CH$_2$)n-OCOR, —(CH$_2$)n-OCOOR, —(CH$_2$)n-OSO$_2$R, —(CH$_2$)n-OSO$_3$R, and —(CH$_2$)n-OSiR$_3$; wherein n is selected from 0, 1, 2, 3 and 4, and each R is independently selected from H, C$_{1-6}$ alkyl, C$_{1-6}$ haloalkyl, C$_{6-10}$ aryl, and (C$_{6-10}$)aryl(C$_{1-6}$)alkyl.

Compounds of formula (II), and salts or solvates thereof, are intermediates in the synthesis of compounds of formula (I) as defined herein, such as obeticholic acid.

Therefore, in another aspect the invention is directed to a process for preparing a compound of formula (I) or a salt or solvate thereof

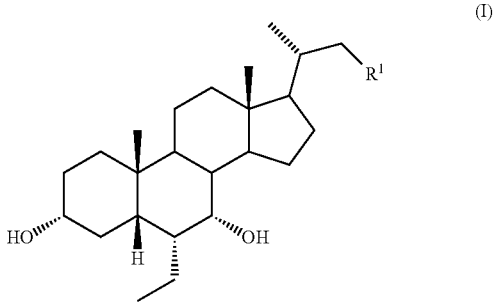

wherein $R^1$ is selected from the group consisting of —(CH$_2$)n-OR, —(CH$_2$)n-COOR, —(CH$_2$)n-CONR$_2$, —(CH$_2$)n-CH(COOR)$_2$, —(CH$_2$)n-CN, —(CH$_2$)n-halogen, —(CH$_2$)n-OCOR, —(CH$_2$)n-OCOOR, —(CH$_2$)n-OSO$_2$R, —(CH$_2$)n-OSO$_3$R, and —(CH$_2$)n-OSiR$_3$; wherein n is selected from 0, 1, 2, 3 and 4, and each R is independently selected from H, C$_{1-6}$ alkyl, C$_{1-6}$ haloalkyl, C$_{6-10}$ aryl, and (C$_{6-10}$)aryl(C$_{1-6}$)alkyl;

which comprises:

(a) hydrogenation of the double bond and reductive opening of the epoxide of compound of formula (II) or a salt or solvate thereof

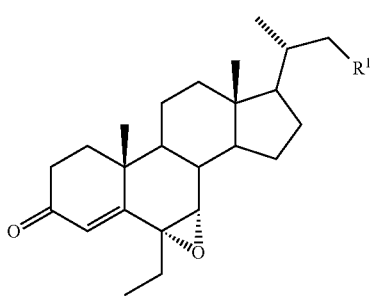

(II)

wherein R¹ is as defined above, to obtain a compound of formula (IIIa) and/or a compound of formula (IIIb), or a salt or solvate thereof

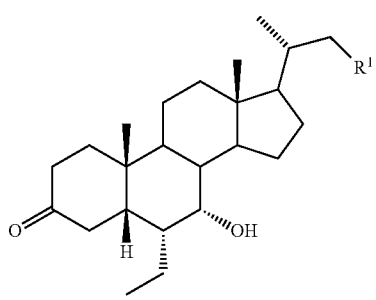

(IIIa)

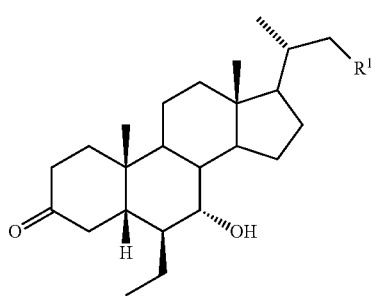

(IIIb)

wherein R¹ is as defined above, and (b) conversion of a compound of formula (IIIa) and/or a compound of formula (IIIb), or a salt or solvate thereof, into a compound of formula (I), or a salt or solvate thereof.

In another aspect, the invention is directed to above mentioned compounds of formula (IIIa), salts or solvates thereof, as well as to compounds of formula (VI) and (VII) disclosed herein below, salts or solvates thereof, which are useful intermediates in the synthesis of compounds of formula (II).

BRIEF DESCRIPTION OF DRAWINGS

FIG. 1. Scheme with processes for preparing compounds of formula (I) according to the invention.

DETAILED DESCRIPTION OF THE INVENTION

The term "halogen" refers to bromine, chlorine, iodine or fluorine.

The term "alkyl" refers to a linear or branched alkane derivative containing from 1 to 6 ("$C_1$-$C_6$ alkyl"), preferably from 1 to 3 ("$C_1$-$C_3$ alkyl"), carbon atoms and which is bound to the rest of the molecule through a single bond. Illustrative examples of alkyl groups include methyl, ethyl, n-propyl, i-propyl, n-butyl, i-butyl, t-butyl, pentyl, hexyl. Preferably, it is methyl or ethyl.

The term "haloalkyl" refers to an alkyl group as defined above containing from 1 to 6 ("$C_1$-$C_6$ haloalkyl"), preferably from 1 to 3 ("$C_1$-$C_3$ haloalkyl"), carbon atoms wherein at least one hydrogen atom has been replaced by halogen. Examples of haloalkyl groups include but are not limited to $CF_3$, $CCl_3$, $CHF_2$, $CF_2CF_3$. Preferably haloalkyl refers to —$CF_3$.

The term "aryl" refers to an aromatic group having between 6 and 10, preferably 6 or 10 carbon atoms, comprising 1 or 2 aromatic nuclei fused to one another. Illustrative examples of aryl groups include phenyl, naphthyl, indenyl, phenanthryl, etc. Preferably, it is phenyl The term "($C_6$-$C_{10}$)aryl($C_1$-$C_6$)alkyl" refers to an alkyl group as defined above substituted with an aryl group as defined above. Examples of such groups include benzyl, phenylethyl, phenylpropyl, naphthylmethyl, etc. Preferably, it is benzyl.

The term "$C_3$-$C_7$ cycloalkyl" refers to a radical derived from cycloalkane containing from 3 to 7, preferably from 3 to 6 ("$C_3$-$C_6$ cycloalkyl") carbon atoms. Illustrative examples of cycloalkyl groups include cyclopropyl, cyclobutyl, cyclopentyl, cyclohexyl, etc.

The term "heterocyclyl" refers to a saturated or partially unsaturated monocyclic or bicyclic system containing from 3 to 10, preferably 5 to 7, ring atoms containing one or more, specifically one, two, three or four ring heteroatoms independently selected from N, O, and S, and the remaining ring atoms being carbon.

The term "heteroaryl" refers to an aromatic monocyclic or bicyclic system containing from 3 to 10, preferably 5 to 7, ring atoms containing one or more, specifically one, two, three or four ring heteroatoms independently selected from O, N and S, and the remaining ring atoms being carbon.

As understood in this technical area, there may be a certain degree of substitution in the aforementioned radicals. Therefore, there may be substitution in any of the groups of the present invention. The previous groups can be substituted in one or more available positions with one or more substituents. Said substituents include, for example and in non-limiting sense, $C_{1-6}$ alkyl, $C_{3-7}$ cycloalkyl, $C_6$-$C_{10}$ aryl, 3- to 10-membered heterocyclyl, 3- to 10-membered heteroaryl, halogen, —CN, $NO_2$, $CF_3$, —$N(R_a)(R_b)$, —$OR_c$, —$SR_d$, —$C(O)R_e$, —$C(O)OR_f$, —$C(O)N(R_g)(R_h)$, —OC(O)$R_i$; wherein $R_a$, $R_b$, $R_c$, $R_d$, $R_e$, $R_f$, $R_g$, $R_h$ and $R_i$ are independently selected from hydrogen, $C_1$-$C_6$ alkyl, $C_6$-$C_{10}$ aryl, 3- to 10-membered heterocyclyl, 3- to 10-membered heteroaryl and trifluoromethyl.

The invention also provides "salts" of the compounds described in the present description. By way of illustration, said salts can be base addition salts or metal salts, and can be synthesized from the parent compounds containing an acid moiety by means of conventional chemical processes known in the art. Such salts are generally prepared, for example, by reacting the free acid form of said compounds with a stoichiometric amount of the suitable base in water or in an organic solvent or in a mixture of the two. Non-aqueous media such as ether, ethyl acetate, ethanol, acetone, isopropanol or acetonitrile are generally preferred. Illustrative examples of base addition salts include inorganic base salts such as, for example, ammonium salts and organic base salts such as, for example, ethylenediamine, ethanolamine, N,N-dialkylenethanolamine, triethanolamine, glutamine, amino acid basic salts, etc. Illustrative examples of metal salts include, for example, sodium, potassium, calcium, magnesium, aluminum and lithium salts. In a particular embodiment, the salt is a metal salt, such as sodium salt.

The term "solvate" according to this invention is to be understood as meaning any form of the compound which has another molecule (most likely a polar solvent) attached to it via non-covalent bonding. Examples of solvate include hydrates and alcoholates, e.g. methanolates.

The term "organic solvent" includes for example cyclic and acyclic ethers (e.g. $Et_2O$, $iPr_2O$, $tBu_2O$, MeOtBu, 1,4-dioxane, tetrahydrofuran, methyltetrahydrofuran), hydrocarbon solvents (e.g. pentane, hexane, heptane, cyclohexane), halogenated solvents (e.g. dichloromethane, chloroform), aromatic solvents (e.g. toluene, xylene), esters (e.g. EtOAc), nitriles (e.g. acetonitrile), amides (e.g. DMF, DMA), alcohols (e.g. methanol, ethanol, propanol, isopropanol), sulfoxides (DMSO) and mixtures thereof.

In a first aspect, the invention is directed to a process (process of the invention) for preparing a compound of formula (I) or a salt or solvate thereof

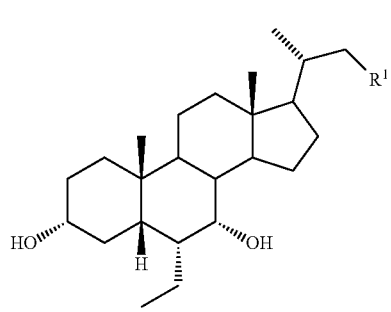

(I)

wherein
R$^1$ is selected from the group consisting of —(CH$_2$)n-OR, —(CH$_2$)n-COOR, —(CH$_2$)n-CONR$_2$, —(CH$_2$)n-CH(COOR)$_2$, —(CH$_2$)n-CN, —(CH$_2$)n-halogen, —(CH$_2$)n-OCOR, —(CH$_2$)n-OCOOR, —(CH$_2$)n-OSO$_2$R, —(CH$_2$)n-OSO$_3$R, and —(CH$_2$)n-OSiR$_3$; wherein n is selected from 0, 1, 2, 3 and 4, and each R is independently selected from H, O$_{1-6}$ alkyl, O$_{1-6}$ haloalkyl, C$_{6-10}$ aryl, and (C$_{6-10}$)aryl(C$_{1-6}$)alkyl;
which comprises:
(a) hydrogenation of the double bond and reductive opening of the epoxide of a compound of formula (II) or a salt or solvate thereof

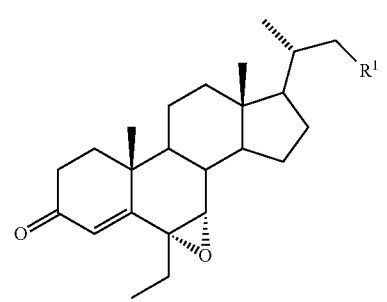

(II)

wherein R$^1$ is as defined above, to obtain a compound of formula (IIIa) and/or a compound of formula (IIIb), or a salt or solvate thereof

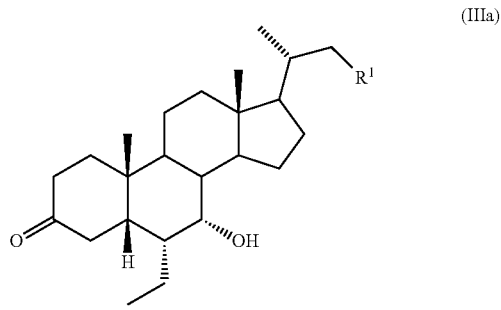

(IIIa)

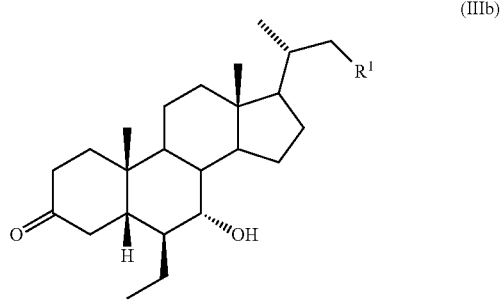

(IIIb)

wherein R$^1$ is as defined above, and
(b) conversion of a compound of formula (IIIa) and/or a compound of formula (IIIb), or a salt or solvate thereof, into a compound of formula (I), or a salt or solvate thereof.

Optionally, this process can further comprise converting R$^1$ into a different R$^1$ group after step (a) and/or after step (b).

In an embodiment, R$^1$ is selected from the group consisting of —(CH$_2$)n-OR, —(CH$_2$)n-COOR, —(CH$_2$)n-CH(COOR)$_2$, —(CH$_2$)n-halogen, —(CH$_2$)n-OCOR, —(CH$_2$)n-OCOOR, —(CH$_2$)n-OSO$_2$R, —(CH$_2$)n-OSO$_3$R; wherein n is selected from 0, 1, 2 and 3, and each R is independently selected from H, C$_{1-6}$ alkyl, C$_{1-6}$ haloalkyl, C$_{6-10}$ aryl, and (C$_{6-10}$)aryl(C$_{1-6}$)alkyl. Preferably, n is selected from 0, 1 and 2.

Preferably, R$^1$ is selected from the group consisting of —OH, halogen, —OCOR, —OSO$_2$R, —CH(COOH)$_2$, —CH(COOR)$_2$, —CH$_2$—COOH and —CH$_2$—COOR, wherein each R is independently selected from C$_{1-6}$ alkyl, C$_{1-6}$ haloalkyl, C$_{6-10}$ aryl, and (C$_{6-10}$)aryl(C$_{1-6}$)alkyl. More preferably, R$^1$ is selected from the group consisting of —OH, —OTs, —OTf, —OMs, —OAc, halogen, —CH(COOR)$_2$, and —CH$_2$—COOR; wherein each R is independently selected from H and C$_{1-6}$ alkyl. Even more preferably, R$^1$ is selected from the group consisting of —OH, —OTs, —OTf, —OMs, —OAc, —CH(COOH)$_2$, —CH(COOMe)$_2$, —CH(COOEt)$_2$, —CH$_2$—COOH, —CH$_2$—COOMe and —CH$_2$—COOEt.

In an embodiment, the compound of formula (I) is Obeticholic acid, INT-767 or ECDCOH, or a salt or solvate thereof. Preferably, it is obeticholic acid or a salt or solvate thereof.

Importantly, compounds of formula (II) are very versatile intermediates for the synthesis of obeticholic acid and derivatives thereof. Depending on the reaction conditions of step (a), the stereochemistry of the carbon atom at position 6 can be controlled. Consequently, compounds of formula (IIIa) can be directly obtained from compounds of formula (II) thus providing a very straightforward synthesis of obeticholic acid and related compounds, without the need of epimerization reactions. Alternatively, if desired, compounds of formula (IIIb) can be also selectively obtained from compounds of formula (II). These compounds can be also converted into obeticholic acid and related compounds or can be used as intermediates in the synthesis of the corresponding epimers at position 6.

In step (a), a compound of formula (II) is converted into a compound of formula (IIIa) or (IIIb) or a mixture thereof by for example a hydrogenation type reaction. In an embodiment, this reaction is carried out in the presence of a catalyst. Suitable catalysts include Pd/C, Pd/CaCO$_3$, Pd/Al$_2$O$_3$, Pd/BaCO$_3$, Pd$_2$(dba)$_3$, Pd(PPh$_3$)$_4$, Pt/C, Pt/Al$_2$O$_3$, PtO$_2$ and Ra—Ni. The catalyst may be present in an amount between 2 and 20 wt %, preferably between 5 and 10 wt %, with respect to the amount of compound of formula (II). The reaction may be carried out in the presence of an organic solvent, such as an ether (e.g. Et$_2$O, iPr$_2$O, tBu$_2$O, MeOtBu, 1,4-dioxane, THF, methyltetrahydrofuran), an ester (e.g. EtOAc), an amide (e.g. DMF, DMA), an alcohol (e.g. methanol, ethanol, propanol, isopropanol), a nitrile (e.g. acetonitrile), and mixtures thereof. Optionally, the reaction may be carried out in the presence of a base, such as an amine, including primary, secondary and tertiary amines such as methyl-, ethyl-, propyl- or butylamine, dimethyl-, diethyl-, dipropyl- or dibutylamine, trimethyl-, triethyl-, tripropyl- or tributylamine, DIPEA, pyridine, 4-dimethylaminopyridine (DMAP), 2-methylpyridine, 4-methylpyridine, 2,4-dimethylpyridine, 2,6-dimethylpyridine, 2,4,6-trimethylpyridine, 2,3,5-trimethylpyridine, 2,6-ditertbutyl-4-methylpyridine, quinaldine, 2,4-dimethylquinoline, and mixtures thereof; and/or in the presence of a phosphine, such as PPh$_3$ or a tri(C$_{1-6}$)alkylphosphine.

This reaction is carried out in the presence of H$_2$, preferably at a pressure between 1 and 5 atm or between 1 and 3 atm, more preferably at a pressure of about 1 atm. In an embodiment, the reaction is carried out at a temperature between −50° C. and 100° C., preferably −20° C. and 90° C., more preferably between −10° C. and 90° C. Sources of hydrogen include H$_2$, formic acid or a salt thereof, and cyclohexene.

In a particular embodiment, the hydrogenation reaction is carried out in the presence of a catalyst, such as Pd/C, Pd/CaCO$_3$, Pd/Al$_2$O$_3$, Pd/BaCO$_3$, Pd$_2$(dba)$_3$, Pd(PPh$_3$)$_4$, Pt/C, Pt/Al$_2$O$_3$, PtO$_2$ or Ra—Ni and an organic solvent, such as an ether (e.g. Et$_2$O, iPr$_2$O, tBu$_2$O, MeOtBu, 1,4-dioxane, THF, methyltetrahydrofuran), an ester (e.g. EtOAc), an amide (e.g. DMF, DMA), an alcohol (e.g. methanol, ethanol, propanol, isopropanol), a nitrile (e.g. acetonitrile) or mixtures thereof, at a temperature between −50° C. and 100° C., preferably −20° C. and 90° C., more preferably between −10° C. and 90° C.

In a particular embodiment, a mixture of a compound of formula (IIIa) and a compound of formula (IIIb), or salts or solvates thereof, is obtained which is separated at this stage or at any further stage of the synthesis.

Depending on the reaction conditions used in step (a), a compound of formula (IIIa) or a compound of formula (IIIb) can be selectively obtained. The term "selectively" in relation to the obtaining of a compound of formula (IIIa) or of formula (IIIb) according to the present invention means that a ratio of the desired isomer with respect to the other isomer of at least 80:20, preferably at least 90:10, more preferably at least 92:8, even more preferably at least 94:6, is obtained.

In an embodiment, a compound of formula (IIIa), or a salt or solvate thereof, is selectively obtained after step (a). In that case, the process of the invention comprises:

(a) hydrogenation of the double bond and reductive opening of the epoxide of a compound of formula (II), or a salt or solvate thereof, to obtain a compound of formula (IIIa), or a salt or solvate thereof, and
(b) reduction of a compound of formula (IIIa), or a salt or solvate thereof, to obtain a compound of formula (I), or a salt or solvate thereof.

The inventors have found that a compound of formula (IIIa), or a salt or solvate thereof, can be selectively obtained in step (a) when the reaction is carried out using Pd/C, Pt/C or PtO$_2$ as catalyst and a base. Suitable bases include pyridine-type bases, such as pyridine, 4-dimethylaminopyridine (DMAP), 2-methylpyridine, 4-methylpyridine, 2,4-dimethylpyridine, 2,6-dimethylpyridine, 2,4,6-trimethylpyridine, 2,3,5-trimethylpyridine, 2,6-ditertbutyl-4-methylpyridine, quinaldine, 2,4-dimethylquinoline, and mixtures thereof. Preferably, the base is selected from pyridine and DMAP; more preferably, it is DMAP.

In an embodiment, the reaction is carried out in the presence of Pd/C, Pt/C or PtO$_2$, an organic solvent and a base. In an embodiment, the organic solvent is selected from an ether (e.g. Et$_2$O, iPr$_2$O, tBu$_2$O, MeOtBu, 1,4-dioxane, THF, methyltetrahydrofuran), an ester (e.g. EtOAc), an amide (e.g. DMF, DMA), an alcohol (e.g. methanol, ethanol, propanol, isopropanol) a nitrile (e.g. acetonitrile) or mixtures thereof; preferably, it is selected from an ether, an alcohol, and mixtures thereof. This reaction may be carried out at a hydrogen pressure between 1 and 5 atm or between 1 and 3 atm, more preferably at a pressure of about 1 atm. In an embodiment, the reaction is carried out at a temperature between −20° C. and 80° C., preferably between 0° C. and 60° C.

In a preferred embodiment, the reaction is carried out in the presence of Pd/C, Pt/C or PtO$_2$, DMAP or pyridine, and an organic solvent. More preferably, in the presence of Pd/C, Pt/C or PtO$_2$, DMAP or pyridine, and an organic solvent, such as an ether (e.g. Et$_2$O, iPr$_2$O, tBu$_2$O, MeOtBu, 1,4-dioxane, THF, methyltetrahydrofuran), an alcohol (e.g. methanol, ethanol, propanol, isopropanol) or mixtures thereof, at a temperature between 0° C. and 60° C.

After preparation of a compound of formula (IIIa), or a salt or solvate thereof, it can be further converted into a compound of formula (I), or a salt or solvate thereof, by reduction of the 3-keto group (step (b)).

Reduction reaction of the 3-keto group to a hydroxyl group can be carried out by conventional means known by the skilled person (e.g. M. B. Smith, J. March, March's Advanced Organic Chemistry, Wiley-Interscience, 5$^{th}$ed., pp. 1197-1203). In an embodiment, the keto group is reduced in the presence of a metallic hydride, or sodium and an alcohol, or a borane, or a silane and a base. Preferably, the reduction is performed in the presence of a metallic hydride (e.g. LiAlH$_4$, LiBH$_4$, LiBHEt$_3$, NaBH$_4$, NaBH(OAc)$_3$, LiAlH(OtBu)$_3$, selectride, Ca(BH$_4$)$_2$), or in the presence of Na and an alcohol (e.g. a C$_1$-C$_6$ aliphatic alcohol such as MeOH, EtOH, nPrOH, iPrOH, nBuOH, sBuOH or tBuOH). In a particular embodiment, the reduction is carried out in the presence of a metallic hydride, preferably NaBH$_4$, LiAlH(OtBu)$_3$, or LiBH$_4$, and optionally a base, preferably an alkali metal hydroxide (e.g. LiOH, NaOH, KOH, CsOH).

The reaction can be carried out in the presence of water, an organic solvent, or mixtures thereof. The reaction is preferably carried out at a temperature between 0° C. and the reflux temperature of the solvent, preferably between 20° C. and 100° C.

Preferably, the reduction is carried out in the presence of NaBH$_4$. In an embodiment, the reduction is carried out in the presence of NaBH$_4$, NaOH and water. In another embodiment, the reduction is carried out in the presence of NaBH$_4$ or LiAlH(OtBu)$_3$ and an organic solvent, such as THF.

In another embodiment, a compound of formula (IIIb), or a salt or solvate thereof, is selectively obtained after step (a). In that case, the process of the invention comprises:

(a) hydrogenation of the double bond and reductive opening of the epoxide of a compound of formula (II), or a salt or solvate thereof, to obtain a compound of formula (IIIb), or a salt or solvate thereof, and (b) conversion of a compound of formula (IIIb), or a salt or solvate thereof, into a compound of formula (I), or a salt or solvate thereof.

The inventors have found that a compound of formula (IIIb), or a salt or solvate thereof, can be selectively obtained in step (a) when the reaction is carried out using Pd/CaCO$_3$, Pd/Al$_2$O$_3$, Pd/BaCO$_3$, Pd/C, Pd$_2$(dba)$_3$ or Pd(PPh$_3$)$_4$ as catalyst. In an embodiment, the reaction is carried out in the presence of a phosphine, such as PPh$_3$ or a tri(C$_{1-6}$)alkyl phoshine. When the reaction is carried out in the presence of Pd/CaCO$_3$, Pd/Al$_2$O$_3$, Pd/BaCO$_3$ or Pd/C, it is preferably carried out in the absence of a base. When the reaction is carried out in the presence of Pd$_2$(dba)$_3$ or Pd(PPh$_3$)$_4$ it is preferably carried out in the presence of a phosphine, such as PPh$_3$ or a tri(C$_{1-6}$)alkyl phoshine and a base, such as a tertiary amine (e.g. Me$_3$N, Et$_3$N, DIPEA) or an inorganic base (e.g. Al$_2$O$_3$). In an embodiment, the reaction is carried out in the presence of Pd/CaCO$_3$, Pd/Al$_2$O$_3$, Pd/BaCO$_3$ or Pd/C and an organic solvent. In another embodiment, the reaction is carried out in the presence of Pd$_2$(dba)$_3$ or Pd(PPh$_3$)$_4$, a phosphine, preferably PPh$_3$, and a base, preferably Me$_3$N, Et$_3$N or DIPEA. Preferably, the reaction is carried out in the presence of Pd/CaCO$_3$ and an organic solvent, preferably DMF. This reaction may be carried out at a hydrogen pressure between 1 and 5 atm or between 1 and 3 atm, more preferably at a pressure of about 1 atm. In an embodiment, the reaction is carried out at a temperature between −20° C. and 100° C., preferably between 0° C. and 100° C.

In an embodiment, conversion of a compound of formula (IIIb), or a salt or solvate thereof, into a compound of formula (I), or a salt or solvate thereof, comprises:

oxidation of a compound of formula (IIIb), or a salt or solvate thereof, to obtain a compound of formula (IV) or a salt or solvate thereof

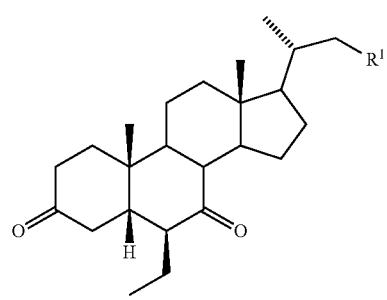

(IV)

wherein R$^1$ is as defined above,
epimerization of a compound of formula (IV), or a salt or solvate thereof, to obtain a compound of formula (V) or a salt or solvate thereof

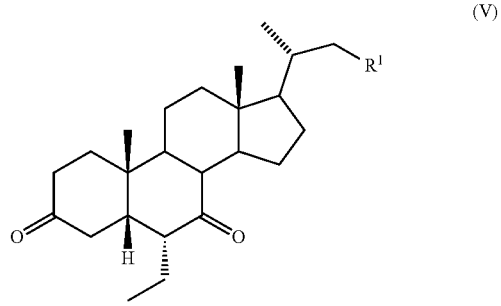

(V)

wherein R$^1$ is as defined above, and
reduction of a compound of formula (V), or a salt or solvate thereof, to a compound of formula (I), or a salt or solvate thereof.

Oxidation of a compound of formula (IIIb), or a salt or solvate thereof, to a compound of formula (IV), or a salt or solvate thereof, can be carried out as described in WO 2016/079517 or by any conventional means known by the skilled person (e.g. M. B. Smith, J. March, March's Advanced Organic Chemistry, Wiley-Interscience, 5$^{th}$ ed., pp. 1514-1517). In an embodiment, the reaction is carried out in the presence of an oxidizing agent. Suitable oxidizing agents include K$_2$Cr$_2$O$_7$, KMnO$_4$, MnO$_2$, CrO$_3$, RuO$_4$, NaClO, pyridinium chlorochromate, pyridinium dichromate, TEMPO, Dess-Martin reagent, Jones reagent, Collins reagent and the like. The reaction can be carried out in the presence of water, an organic solvent, or mixtures thereof and is preferably carried out at a temperature between 0° C. and the reflux temperature of the solvent, preferably between 0° C. and 40° C.

Epimerization of a compound of formula (IV), or a salt or solvate thereof, to obtain a compound of formula (V), or a salt or solvate thereof, can be carried out as described in EP 1888614 B1, WO 2016/079517 or by any other conventional means known by the skilled person. In an embodiment, epimerization is carried out by heat treatment or by treatment with a base. The reaction can be carried out in the presence of water, an organic solvent, or mixtures thereof. Preferably, the reaction is carried out in the presence of an organic solvent.

In a particular embodiment, epimerization is carried out by heat treatment, preferably at a temperature between 50 and 120° C., more preferably between 80 and 110° C.

In another embodiment, epimerization is carried out in the presence of a base. Suitable bases include alkali metal hydroxides (e.g. LiOH, NaOH, KOH, CsOH) and alkali metal alcoholates (e.g. NaOMe, NaOEt, NaOiPr, NaOnBu, NaOtBu, KOMe, KOEt, KOiPr, KOnBu, KOtBu). The reaction is preferably carried out in the presence of an alcohol, preferably a C$_1$-C$_6$ aliphatic alcohol. The reaction can be carried out at a temperature between 0° C. and the reflux temperature of the solvent, preferably between 0° C. and 40° C.

Suitable reaction conditions for the reduction of a compound of formula (V), or a salt or solvate thereof, to a compound of formula (I), or a salt or solvate thereof, are as defined above for the reduction of a compound of formula (IIIa) to a compound of formula (I).

Compounds of formula (II), salts or solvates thereof, may be prepared by a process comprising epoxidation of a compound (VI) or a salt or solvate thereof

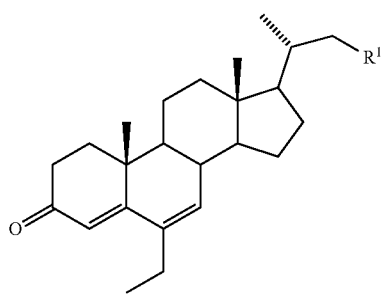

(VI)

wherein R¹ is as defined above.

In an embodiment, epoxidation reaction is carried out in the presence of a peroxycarboxylic acid, hydrogen peroxide or oxone, preferably a peroxycarboxylic acid such as mCPBA, benzoic acid, monoperphthalic acid, or MMPP. The reaction may be carried out in the presence of an organic solvent, and may be carried out at a temperature between −40° C. and the reflux temperature of the solvent, preferably between −20° C. and 40° C. In an embodiment, the reaction is carried out in the presence of mCPBA and a halogenated solvent, such as chloroform or dichloromethane.

Compounds of formula (VI), salts or solvates thereof, may be prepared by a process comprising isomerization of a compound (VII) or a salt or solvate thereof

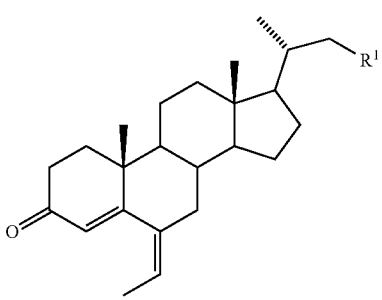

(VII)

wherein R¹ is as defined above.

In an embodiment, isomerization is carried out in the presence of a transition metal catalyst, such as Pd, Ni, Pt, Rh or Ru, preferably a Pd based catalyst. Suitable catalysts include Pd/C, $PdCl_2$, $Pd(OAc)_2$, $P(PPh_3)_4$, $Pd(O_2CCF_3)_2$, $Pd(CH_3CN)_2(PPh_3)_2$, $Pd(CH_3CN)_2Cl_2$, $Pd_2(dba)_3$, $Pd(dba)_2$, $Pd(allyl)_2Cl_2$, $[Pd(allyl)Cl]_2$, Rh/C, $RhCl(PPh_3)_3$, Ru/C, $RuCl_2(PPh_3)_3$, $[Ni(allyl)Br]_2$. The reaction is preferably carried out in the presence of an organic solvent, and is preferably carried out at a temperature between −20° C. and the reflux temperature of the solvent, more preferably between 20° C. and 100° C. In an embodiment, the reaction is carried out in the presence of Pd/C and an alcohol, such as methanol, ethanol, propanol or isopropanol; preferably in the presence of Pd/C, AcONa, cyclohexene and ethanol.

Compounds of formula (VII), salts or solvates thereof, may be prepared from compounds of formula (I), salts or solvates thereof

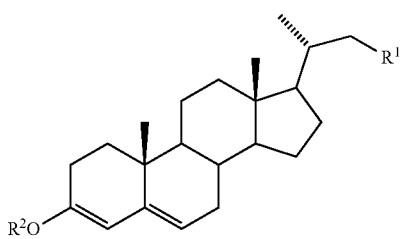

(IX)

wherein R¹ is as defined above and R² is selected from $C_{1-6}$ alkyl, $C_{6-10}$ aryl, $(C_{6-10})$aryl$(C_{1-6})$alkyl, COR' and $SiR'_3$, wherein each R' is independently selected from $C_{1-6}$ alkyl, $C_{6-10}$ aryl and $C_{1-6}$ alkoxy.

Compounds of formula (VII), salts or solvates thereof, may be prepared by a process comprising:

formylation of a compound of formula (IX), or a salt or solvate thereof, to provide a compound of formula (VIII) or a salt or solvate thereof

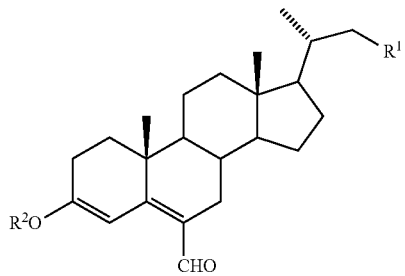

(VIII)

wherein R¹ and R² are as defined above, and methylation followed by dehydration of a compound of formula (VIII), or a salt or solvate thereof, to provide a compound of formula (VII), or a salt or solvate thereof.

Formylation reaction may carried out using the Vilsmeier reaction, in the presence of an N,N-disubstituted formamide, such as DMF or N-methylformanilide, and a chloride reagent, such as $POCl_3$, phosgene, or cyanuric chloride. Preferably, the reaction is carried out in the presence of an N,N-disubstituted formamide and a chloride reagent, more preferably in the presence of DMF and $POCl_3$. The reaction may be carried out in the presence of an organic solvent, and may be carried out at a temperature between −40° C. and the reflux temperature of the solvent, preferably between −20° C. and 30° C.

Methylation of a compound of formula (VIII), or a salt or solvate thereof, may be carried out by reaction with MeMgCl, MeMgBr or MeLi, preferably in the presence of an organic solvent, such as an ether (e.g. $Et_2O$, $iPr_2O$, $tBu_2O$, MeOtBu, 1,4-dioxane, tetrahydrofuran, methyltetrahydrofuran). The reaction may be carried out at a temperature between −40° C. and the reflux temperature of the solvent, preferably between −20° C. and 30° C. In an embodiment, the reaction is carried out in the presence of MeMgCl and an ether at a temperature between −20° C. and 30° C.

After methylation reaction, dehydration of the resulting compound may be carried out by treatment with an acid or a base. Suitable acids include organic acids, inorganic acids, Lewis acids and mixtures thereof. Examples of suitable acids include acetic acid, trifluoroacetic acid, chloroacetic acid, methanesulfonic acid, trifluoromethanesulfonic acid, formic acid, propionic acid, butyric acid, malic acid, citric acid, benzoic acid, p-toluenesulfonic acid, oxalic acid, succinic acid, hydrochloric acid, hydrobromic acid, hydrofluoric acid, perchloric acid, chloric acid, sulfuric acid, nitric acid, phosphoric acid, $ZnCl_2$, $AlCl_3$ and $BF_3$. Suitable bases include e.g. alkali metal hydrides, alkali metal alkoxides, alkali metal hydroxides, such as sodium hydride, potassium hydride, sodium methoxide, sodium ethoxide, sodium t-butoxide, potassium methoxide, potassium ethoxide, potassium t-butoxide, sodium hydroxide and potassium hydroxide. Preferably, the reaction is carried out in the presence of an acid, such as HCl. The reaction may be carried out in the presence of an organic solvent, and may be carried out at a temperature between −40° C. and the reflux temperature of the solvent, preferably between −20° C. and 60° C.

Compounds of formula (VII), salts or solvates thereof, may be also prepared by Mannich type reaction of a compound of formula (IX), or a salt or solvate thereof, followed by elimination of the resulting amine to provide a compound of formula (VII), or a salt or solvate thereof.

Mannich reaction may be carried out in the presence of acetaldehyde and a primary or secondary amine, such as phenyl-, methyl-, ethyl-, propyl- or butylamine, diphenyl-, dimethyl-, diethyl-, dipropyl- or dibutylamine, methylphenylamine or ethylphenylamine. The reaction may be carried out in the presence of an organic solvent and may be carried out at a temperature between −20° C. and the reflux temperature of the solvent, preferably between −20° C. and 100° C.

After Mannich reaction, elimination of the resulting amine may be carried out by treatment with an acid. Suitable acids include organic acids, inorganic acids, Lewis acids and mixtures thereof, such as acetic acid, trifluoroacetic acid, chloroacetic acid, methanesulfonic acid, trifluoromethanesulfonic acid, formic acid, propionic acid, butyric acid, malic acid, citric acid, benzoic acid, p-toluenesulfonic acid, oxalic acid, succinic acid, hydrochloric acid, hydrobromic acid, hydrofluoric acid, perchloric acid, chloric acid, sulfuric acid, nitric acid, phosphoric acid, $ZnCl_2$, $AlCl_3$ and $BF_3$.

Compounds of formula (IX), salts or solvates thereof, may be prepared from a compound (X) or a salt or solvate thereof

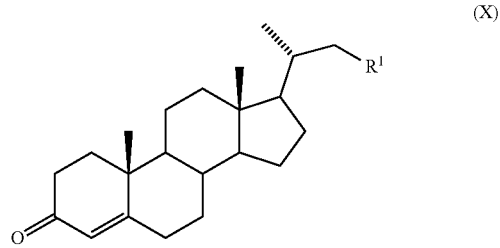

(X)

wherein $R^1$ is as defined above.

This reaction can be carried out by means of well-known processes for the synthesis of enol ether or enol esters. In an embodiment, compounds of formula (IX) wherein $R^2$ is $C_{1-6}$ alkyl are obtained by reaction of a compound of formula (X) with a trialkyl orthoformate in the presence of an acid. Suitable acids include Suitable acids include acetic acid, trifluoroacetic acid, chloroacetic acid, methanesulfonic acid, trifluoromethanesulfonic acid, formic acid, propionic acid, butyric acid, malic acid, citric acid, benzoic acid, p-toluenesulfonic acid, oxalic acid, succinic acid, hydrochloric acid, hydrobromic acid, hydrofluoric acid, perchloric acid, chloric acid, sulfuric acid, nitric acid, phosphoric acid, $ZnCl_2$, $AlCl_3$ and $BF_3$. The reaction may be carried out in the presence of an organic solvent, and may be carried out at a temperature between −20° C. and the reflux temperature of the solvent, preferably between 10° C. and 90° C. In an embodiment, the reaction is carried out in the presence of methyl or ethyl orthoformate, pTsOH and an organic solvent, preferably an alcohol, such as MeOH or EtOH.

In another embodiment, compounds of formula (IX) wherein $R^2$ is $SiR'_3$ are obtained by reaction of a compound of formula (X) with a compound of formula $R'_3SiZ$, wherein each R' is independently selected from $C_{1-6}$ alkyl, $C_{6-10}$ aryl and $C_{1-6}$ alkoxy, and Z is halogen or triflate, in the presence of a base. Suitable bases include lithium bases such as e.g. BuLi, LDA and HMDSLi. The reaction may be carried out in the presence of an organic solvent, and may be carried out at a temperature between −20° C. and the reflux temperature of the solvent.

In another embodiment, compounds of formula (IX) wherein $R^2$ is Ac are obtained by reaction of a compound of formula (X) with isopropenyl acetate, or acetic anhydride or an acetyl halide, in the presence of an acid or a base. Suitable acids include sulfuric acid, perchloric acid, pTsOH and sulfonic acid. Suitable bases include pyridine, DMAP, $Me_3N$, $Et_3N$ and DIPEA. The reaction may be carried out in the presence of an organic solvent and may be carried out at a temperature between 20° C. and the reflux temperature of the solvent, preferably between 40° C. and 120° C.

In an embodiment, the process of the invention comprises converting $R^1$ into a different $R^1$ group at any stage of the synthesis. Methods for converting an $R^1$ group into a different $R^1$ group according to the invention are familiar to those of skill in the art.

For example, when $R^1$ is —$(CH_2)$n-OH, it can be converted into a —$(CH_2)$n-OR, -or a $(CH_2)$n-halogen, or a —$(CH_2)$n-OCOR, or a —$(CH_2)$n-OCOOR, or a —$(CH_2)$n-$OSO_2$R, or a —$(CH_2)$n-$OSO_3$R, or a —$(CH_2)$n-$OSiR_3$ group by well-known methods. For instance, by reaction with a halogen source, with an ester or acyl halide, with an anhydride, with a halosulfonate, or with chlorosulfuric acid or a chlorosulfuric acid ester, or with a halosilane, respectively.

When $R^1$ is —$(CH_2)$n-OH, it can be converted into the corresponding acid or ester group by oxidation and optionally esterification.

When $R^1$ is $(CH_2)$n-halogen, —$(CH_2)$n-OCOR, —$(CH_2)$n-OCOOR, —$(CH_2)$n-$OSO_2$R, or —$(CH_2)$n-$OSiR_3$, it can be converted into a —$(CH_2)$n-$CH(COOR)_2$ group by reaction with a compound of formula $CH_2(COOR)_2$. This reaction can be carried out in the presence of a base such as an alkali metal hydride, preferably NaH, and an organic solvent, preferably an ether, such as $Et_2O$, $iPr_2O$, $tBu_2O$, MeOtBu, 1,4-dioxane, tetrahydrofuran or methyltetrahydrofuran. The reaction may be carried out at a temperature between 0° C. and 100° C., preferably between 20° C. and 100° C., more preferably between 40° C. and 80° C.

When $R^1$ is —$(CH_2)$n-$CH(COOR)_2$ it can be converted into a —$(CH_2)$n-$CH_2$—COOH group by, if needed, hydrolysis of the esters groups (i.e. if R is not H) to obtain a group —$(CH_2)$n-$CH(COOH)_2$, and decarboxylation. Hydrolysis of the ester groups may be carried out in the presence of water and an acid or a base. Suitable acids include acetic acid, trifluoroacetic acid, methanesulfonic acid, trifluoromethanesulfonic acid, hydrochloric acid, hydrobromic acid, hydrofluoric acid, perchloric acid, sulfuric acid, nitric acid, phosphoric acid, formic acid, propionic acid, butyric acid, malic acid, citric acid, benzoic acid, p-toluenesulfonic acid, oxalic acid and succinic acid, preferably hydrochloric acid, hydrobromic acid and sulfuric acid. Suitable bases include alkali metal alkoxides and alkali metal hydroxides, such as NaOEt, NaOMe, NaOtBu, KOEt, KOMe, KOtBu, NaOH, LiOH, KOH, CsOH, preferably NaOH, KOH and NaOMe, more preferably NaOH. The reaction may be carried out at a temperature between 20° C. and the reflux temperature of the solvent, preferably between 40° C. and 100° C., more preferably between 80° C. and 100° C. Decarboxylation reaction may be carried out under heat treatment, preferably at a temperature between 60° C. and 150° C. In an embodiment, the decarboxylation reaction is carried out in xylene, toluene, pyridine or water. In a particular embodiment, the decarboxylation reaction is carried out at a temperature between 60° C. and 150° C., and more particularly under reflux, in xylene or toluene. In another embodiment, the decarboxylation reaction is carried out at a temperature between 60° C. and 150° C., and more particularly under reflux, in pyridine or water.

When $R^1$ is $-(CH_2)n-COOH$ it can be converted into the corresponding alcohol, ester or amide by reduction, or by esterification, or by treatment with an amine, respectively.

In a particular embodiment, the invention is directed to a process for preparing obeticholic acid, or a salt or solvate thereof, which comprises:

(a) hydrogenation of the double bond and reductive opening of the epoxide of a compound of formula (II') or a salt or solvate thereof

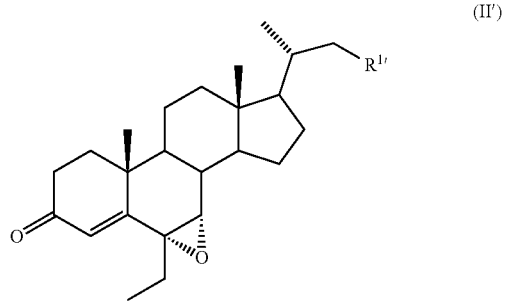

(II')

wherein $R^{1'}$ is selected from the group consisting of $-OH$, halogen, $-OCOR$, $-OSO_2R$, $-CH(COOH)_2$, $-CH(COOR)_2$, $-CH_2-COOH$ and $-CH_2-COOR$; wherein each R is independently selected from $C_{1-6}$ alkyl, $C_{1-6}$ haloalkyl, $C_{6-10}$ aryl, and $(C_{6-10})aryl(C_{1-6})alkyl$, to obtain a compound of formula (IIIa) or a salt or solvate thereof

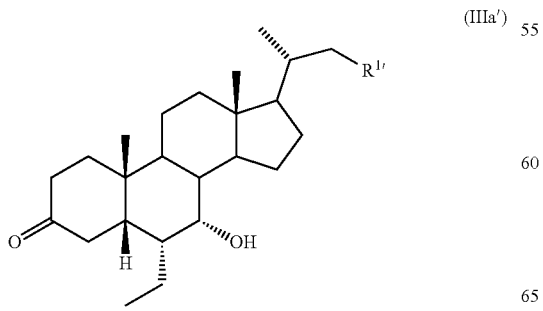

(IIIa')

wherein $R^{1'}$ is as defined above, and (b) conversion of a compound of formula (IIIa), or a salt or solvate thereof, into obeticholic acid, or a salt or solvate thereof, by a process comprising either:

A. if $R^{1'}$ in the compound of formula (IIIa), or a salt or solvate thereof, is $-CH_2-COOH$ or $-CH_2-COOR$, wherein R is selected from $C_{1-6}$ alkyl, $C_{1-6}$ haloalkyl, $C_{6-10}$ aryl, and $(C_{6-10})aryl(C_{1-6})alkyl$:

hydrolysis of the ester groups if $R^{1'}$ is $-CH_2-COOR$, to obtain a compound wherein $R^{1'}$ is $-CH_2-COOH$, and reduction of the ketone group, wherein the reduction of the keto group can be performed before hydrolysis of the ester group, or after hydrolysis of the ester group; or B. if $R^{1'}$ in the compound of formula (IIIa), or a salt or solvate thereof, is $-CH(COOH)_2$ or $-CH(COOR)_2$, wherein R is selected from $C_{1-6}$ alkyl, $C_{1-6}$ haloalkyl, $C_{6-10}$ aryl, and $(C_{6-10})aryl(C_{1-6})alkyl$:

hydrolysis of the ester groups if $R^{1'}$ is $-CH(COOR)_2$, to obtain a compound wherein $R^{1'}$ is $-CH(COOH)_2$, decarboxylation reaction, and reduction of the ketone group, wherein the reduction of the keto group can be performed before hydrolysis of the ester groups, or before decarboxylation reaction, or after decarboxylation reaction; or C. if $R^{1'}$ in the compound of formula (IIIa), or a salt or solvate thereof, is selected from $-OH$, halogen, $-OCOR$, and $-OSO_2R$, wherein R is selected from $C_{1-6}$ alkyl, $C_{1-6}$ haloalkyl, $C_{6-10}$ aryl, and $(C_{6-10})aryl(C_{1-6})alkyl$:

if $R^{1'}$ is $-OH$, conversion into a compound wherein $R^{1'}$ is selected from halogen, $-OCOR$, and $-OSO_2R$, wherein R is selected from $C_{1-6}$ alkyl, $C_{1-6}$ haloalkyl, $C_{6-10}$ aryl, and $(C_{6-10})aryl(C_{1-6})alkyl$, reaction with a compound of formula $CH_2(COOR)_2$ wherein each R is independently selected from $C_{1-6}$ alkyl, $C_{1-6}$ haloalkyl, $C_{6-10}$ aryl and $(O_{6-10})$ aryl($C_{1-6}$)alkyl, to obtain a compound wherein $R^{1'}$ is $-CH(COOR)_2$, hydrolysis of the ester groups, decarboxylation reaction, and reduction of the ketone group, wherein the reduction of the keto group can be performed before conversion of $-OH$ into halogen, $-OCOR$, or $-OSO_2R$, or before reaction with a compound of formula $CH_2(COOR)_2$, or before hydrolysis of the ester groups, or before decarboxylation reaction, or after decarboxylation reaction.

In a particular embodiment, the invention is directed to a process for preparing obeticholic acid, or a salt or solvate thereof, which comprises:

(a) hydrogenation of the double bond and reductive opening of the epoxide of a compound of formula (II') or a salt or solvate thereof

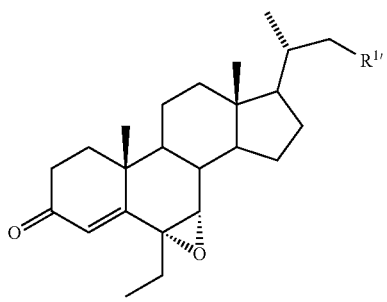

(II')

wherein R[1'] is selected from the group consisting of —OH, halogen, —OCOR and —OSO$_2$R, wherein each R is independently selected from $C_{1-6}$ alkyl, $C_{1-6}$ haloalkyl, $C_{6-10}$ aryl, and $(C_{6-10})$aryl$(C_{1-6})$alkyl, to obtain a compound of formula (IIIa) or a salt or solvate thereof

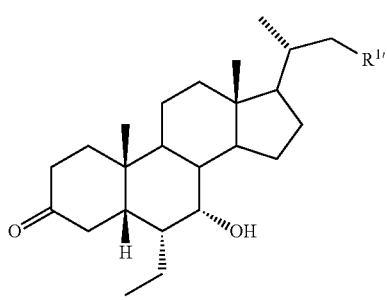

(IIIa')

wherein R[1'] is as defined above, and
(b) conversion of a compound of formula (IIIa), or a salt or solvate thereof, into obeticholic acid, or a salt or solvate thereof, by a process comprising:
reduction of the ketone group,
reaction with a compound of formula CH$_2$(COOR)$_2$ wherein each R is independently selected from $C_{1-6}$ alkyl, $C_{1-6}$ haloalkyl, $C_{6-10}$ aryl and $(C_{6-10})$aryl$(C_{1-6})$alkyl, to obtain a compound wherein R[1'] is —CH(COOR)$_2$,
hydrolysis of the ester groups, and
decarboxylation reaction.

In an embodiment, the process for preparing obeticholic acid, or a salt or solvate thereof, further comprises epoxidation of a compound (VI') or a salt or solvate thereof

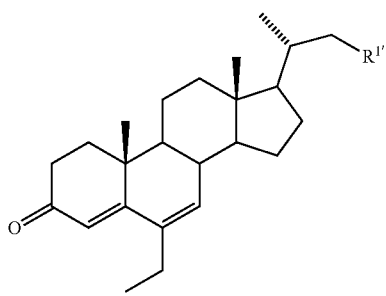

(VI')

wherein R[1'] is as defined above, to obtain a compound of formula (II'), or a salt or solvate thereof.

In an embodiment, the process for preparing obeticholic acid, or a salt or solvate thereof, further comprises isomerization of a compound (VI') or a salt or solvate thereof

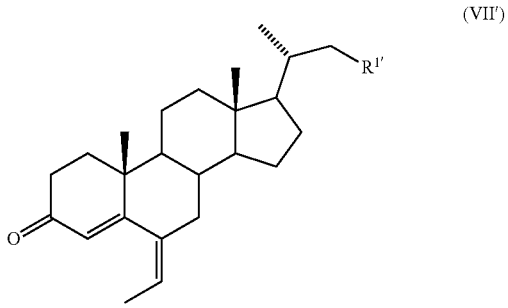

(VII')

wherein R[1'] is as defined above, to obtain a compound of formula (VI'), or a salt or solvate thereof.

In an embodiment, the process for preparing obeticholic acid, or a salt or solvate thereof, further comprises formylation of a compound (IX') or a salt or solvate thereof

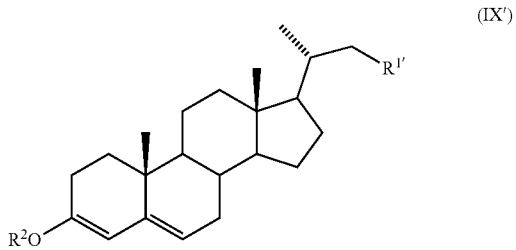

(IX')

wherein R[1'] is as defined above, to obtain a compound of formula (VIII'), or a salt or solvate thereof

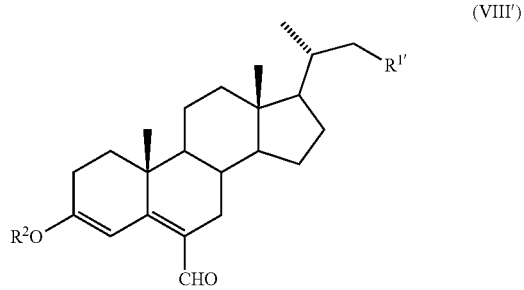

(VIII')

wherein R[1'] is as defined above, and R$^2$ is selected from $C_{1-6}$ alkyl, $C_{6-10}$ aryl, $(C_{6-10})$ aryl$(C_{1-6})$alkyl and SiR'$_3$, wherein each R' is independently selected from $C_{1-6}$ alkyl, $C_{6-10}$ aryl and $C_{1-6}$ alkoxy; and methylation followed by dehydration of a compound of formula (VIII'), or a salt or solvate thereof, to provide a compound of formula (VII'), or a salt or solvate thereof.

In an embodiment, the process for preparing obeticholic acid, or a salt or solvate thereof, further comprises enol ether formation of a compound (X') or a salt or solvate thereof

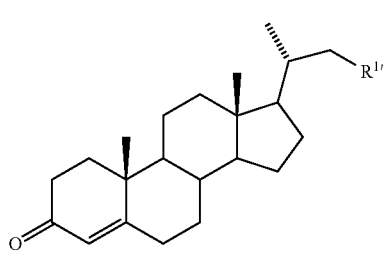
(X')

wherein R¹' is as defined above.

In a particular embodiment, the compound of formula (X') is 3-keto-bisnorcholenol.

Suitable and preferred reaction conditions for each of the steps for the process of preparing obeticholic acid, or a salt or solvate thereof, are as defined above for the process of the invention.

The invention is also directed to a compound of formula (II) or a salt or solvate thereof

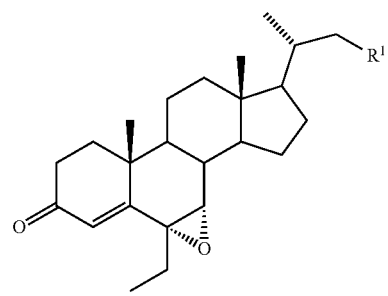
(II)

wherein $R^1$ is selected from the group consisting of —(CH$_2$)n-OR, —(CH$_2$)n-COOR, —(CH$_2$)n-CONR$_2$, —(CH$_2$)n-CH(COOR)$_2$, —(CH$_2$)n-CN, —(CH$_2$)n-halogen, —(CH$_2$)n-OCOR, —(CH$_2$)n-OCOOR, —(CH$_2$)n-OSO$_2$R, —(CH$_2$)n-OSO$_3$R, and —(CH$_2$)n-OSiR$_3$; wherein n is selected from 0, 1, 2, 3 and 4, and each R is independently selected from H, C$_{1-6}$ alkyl, C$_{1-6}$ haloalkyl, C$_{6-10}$ aryl, and (C$_{6-10}$)aryl(C$_{1-6}$)alkyl.

Preferably, $R^1$ is selected from the group consisting of halogen, —OCOR, —OSO$_2$R, —CH(COOH)$_2$, —CH(COOR)$_2$, —CH$_2$—COOH and —CH$_2$—COOR; wherein each R is independently selected from C$_{1-6}$ alkyl, C$_{1-6}$ haloalkyl, C$_{6-10}$ aryl, and (C$_{6-10}$)aryl(C$_{1-6}$)alkyl. More preferably, each R is independently selected from C$_{1-6}$ alkyl, C$_{1-6}$ haloalkyl, C$_{6-10}$ aryl, and (C$_{6-10}$)aryl(C$_{1-6}$)alkyl.

More preferably, $R^1$ is selected from the group consisting of —OH, —OTs, —OTf, —OMs, —OAc, halogen, —CH(COOR)$_2$, and —CH$_2$—COOR; wherein each R is independently selected from H and C$_{1-6}$ alkyl.

Even more preferably, the compound of formula (II) is selected from the group consisting of:

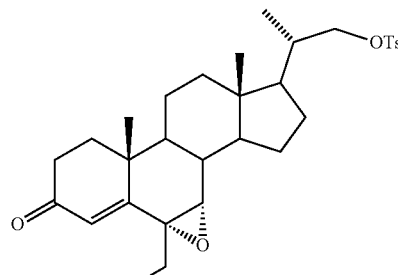

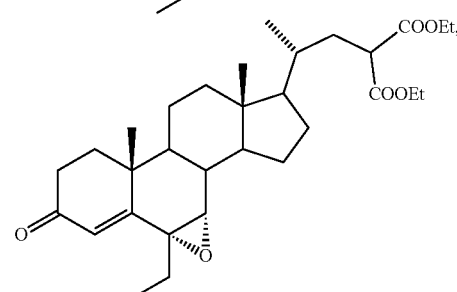

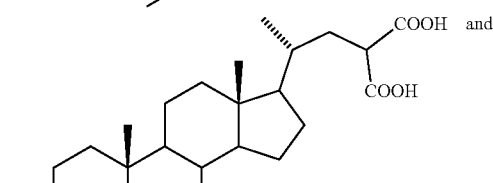

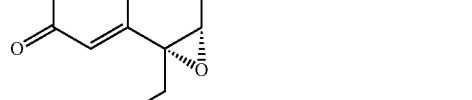

or a salt or solvate thereof.

In another aspect, the invention is directed to a compound of formula (IIIa) or a salt or solvate thereof

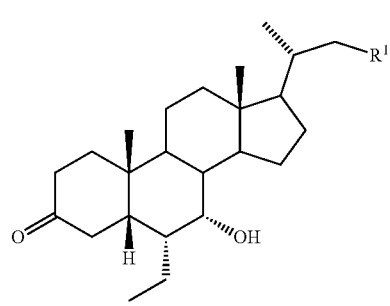
(IIIa)

wherein $R^1$ is selected from the group consisting of —(CH$_2$)n-OR, —(CH$_2$)n-COOR, —(CH$_2$)n-CONR$_2$, —(CH$_2$)n-CH (COOR)₂, —(CH₂)n-CN, —(CH₂)n-halogen, —(CH₂)n-OCOR, —(CH₂)n-OCOOR, —(CH₂)n-OSO₂R, —(CH₂)n-OSO₃R, and —(CH₂)n-OSiR₃; wherein n is selected from 0, 1, 2, 3 and 4, and each R is independently selected from H, C$_{1-6}$ alkyl, C$_{1-6}$ haloalkyl, C$_{6-10}$ aryl, and (C$_{6-10}$)aryl(C$_{1-6}$)alkyl;

provided that R¹ is not —COOH or —CH₂—COOMe.

Preferably, R¹ is selected from the group consisting of halogen, —OCOR, —OSO₂R, —CH(COOH)₂, —CH(COOR)₂, —CH₂—COOH and —CH₂—COOR; wherein each R is independently selected from C$_{1-6}$ alkyl, C$_{1-6}$ haloalkyl, C$_{6-10}$ aryl, and (C$_{6-10}$)aryl(C$_{1-6}$)alkyl; more preferably, each R is independently selected from C$_{1-6}$ alkyl, C$_{1-6}$ haloalkyl, C$_{6-10}$ aryl, and (C$_{6-10}$)aryl(C$_{1-6}$)alkyl; provided that R¹ is not —CH₂—COOMe.

More preferably, R¹ is selected from the group consisting of —OH, —OTs, —OTf, —OMs, —OAc, halogen, —CH(COOR)₂, and —CH₂—COOR'; wherein each R is independently selected from H and C$_{1-6}$ alkyl and R' is selected from H and C$_{2-6}$ alkyl.

Even more preferably, the compound of formula (IIIa) is selected from the group consisting of:

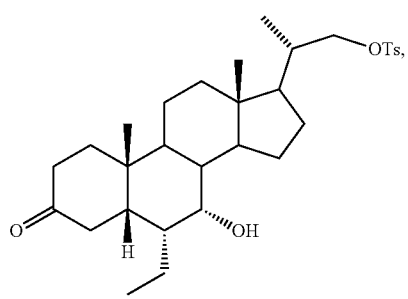

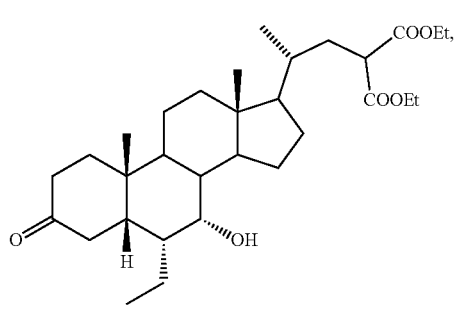

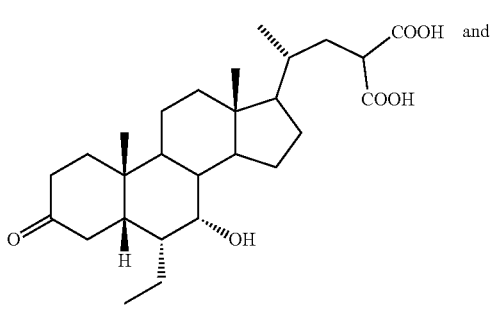

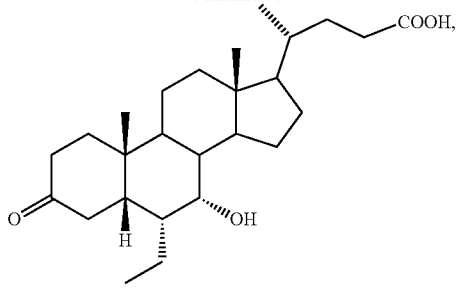

or a salt or solvate thereof.

The invention is also directed to a compound of formula (VI) or a salt or solvate thereof

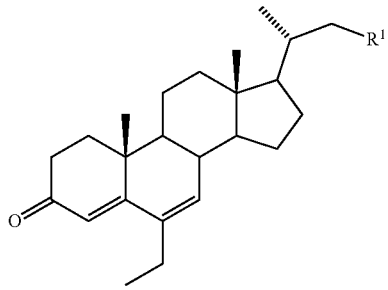

(VI)

wherein
R¹ is selected from the group consisting of —(CH₂)n-OR, —(CH₂)n-COOR, —(CH₂)n-CONR₂, —(CH₂)n-CH(COOR)₂, —(CH₂)n-CN, —(CH₂)n-halogen, —(CH₂)n-OCOR, —(CH₂)n-OCOOR, —(CH₂)n-OSO₂R, —(CH₂)n-OSO₃R, and —(CH₂)n-OSiR₃; wherein n is selected from 0, 1, 2, 3 and 4, and each R is independently selected from H, C$_{1-6}$ alkyl, C$_{1-6}$ haloalkyl, C$_{6-10}$ aryl, and (C$_{6-10}$)aryl(C$_{1-6}$)alkyl.

Preferably, R¹ is selected from the group consisting of halogen, —OCOR, —OSO₂R, —CH(COOH)₂, —CH(COOR)₂, —CH₂—COOH and —CH₂—COOR; wherein each R is independently selected from C$_{1-6}$ alkyl, C$_{1-6}$ haloalkyl, C$_{6-10}$ aryl, and (C$_{6-10}$)aryl(C$_{1-6}$)alkyl. More preferably, each R is independently selected from C$_{1-6}$ alkyl, C$_{1-6}$ haloalkyl, C$_{6-10}$ aryl, and (C$_{6-10}$)aryl(C$_{1-6}$)alkyl.

More preferably, R¹ is selected from the group consisting of —OH, —OTs, —OTf, —OMs, —OAc, halogen, —CH(COOR)₂, and —CH₂—COOR; wherein each R is independently selected from H and C$_{1-6}$ alkyl.

Even more preferably, the compound of formula (VI) is selected from the group consisting of:

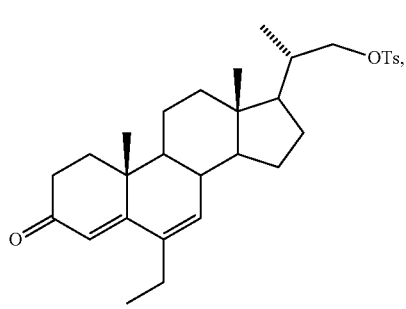

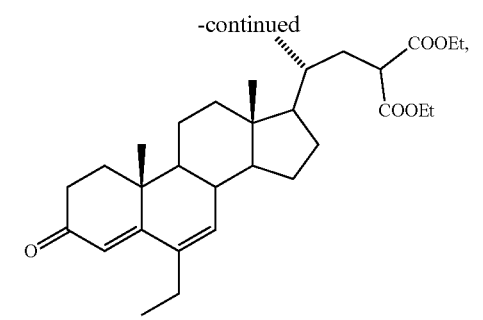

or a salt or solvate thereof.

The invention is also directed to a compound of formula (VII) or a salt or solvate thereof

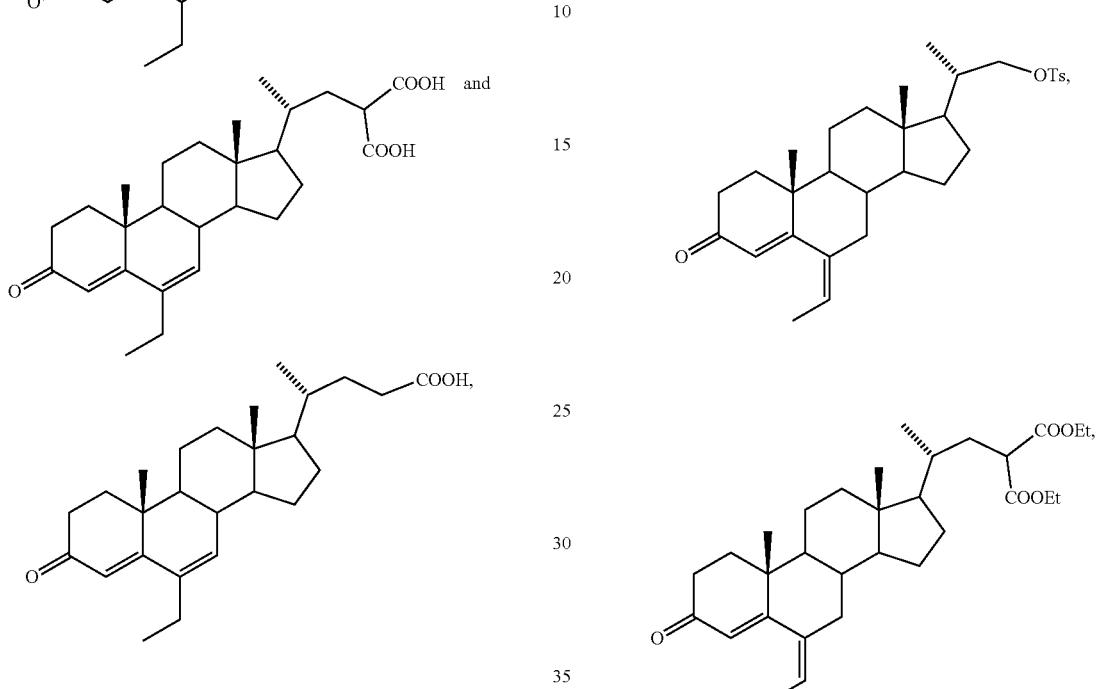

(VII)

wherein

R¹ is selected from the group consisting of —(CH₂)n-OR, —(CH₂)n-COOR, —(CH₂)n-CONR₂, —(CH₂)n-CH(COOR)₂, —(CH₂)n-CN, —(CH₂)n-halogen, —(CH₂)n-OCOR, —(CH₂)n-OCOOR, —(CH₂)n-OSO₂R, —(CH₂)n-OSO₃R, and —(CH₂)n-OSiR₃; wherein n is selected from 0, 1, 2, 3 and 4, and each R is independently selected from H, $C_{1-6}$ alkyl, $C_{1-6}$ haloalkyl, $C_{6-10}$ aryl, and $(C_{6-10})aryl(C_{1-6})$alkyl.

Preferably, R¹ is selected from the group consisting of halogen, —OCOR, —OSO₂R, —CH(COOH)₂, —CH(COOR)₂, —CH₂—COOH and —CH₂—COOR; wherein each R is independently selected from $C_{1-6}$ alkyl, $C_{1-6}$ haloalkyl, $C_{6-10}$ aryl, and $(C_{6-10})aryl(C_{1-6})$alkyl. More preferably, each R is independently selected from $C_{1-6}$ alkyl, $C_{1-6}$ haloalkyl, $C_{6-10}$ aryl, and $(C_{6-10})aryl(C_{1-6})$alkyl.

More preferably, R¹ is selected from the group consisting of —OH, —OTs, —OTf, —OMs, —OAc, halogen, —CH(COOR)₂, and —CH₂—COOR; wherein each R is independently selected from H and $C_{1-6}$ alkyl.

Even more preferably, the compound of formula (VII) is selected from the group consisting of:

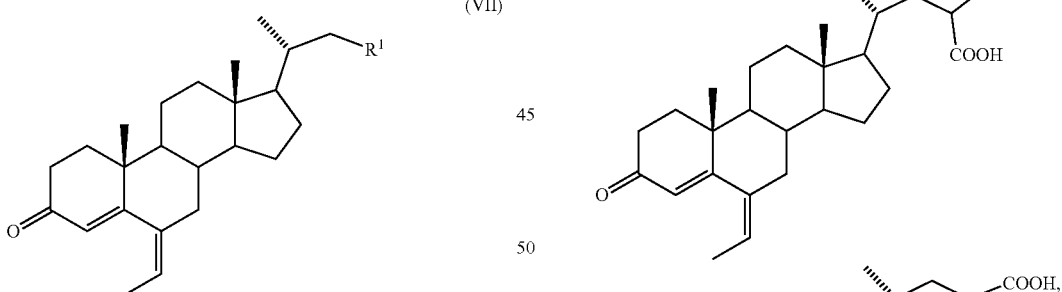

or a salt or solvate thereof.

It should be understood that the scope of the present disclosure includes all the possible combinations of embodiments disclosed herein.

EXAMPLES
Example 1: Synthesis of Obeticholic Acid from 3-Keto-Bisnorcholenol
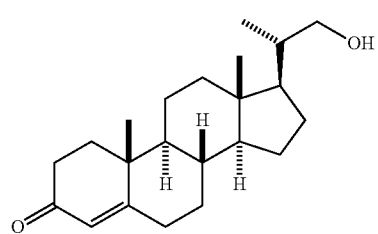
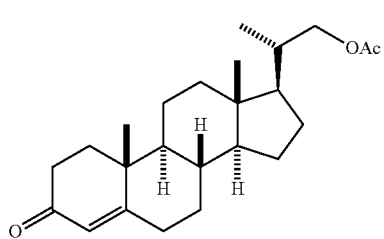
1
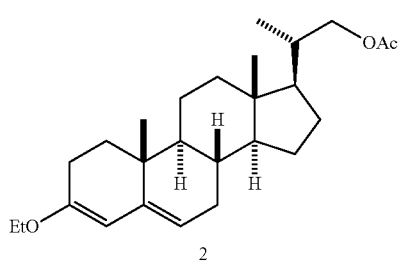
2
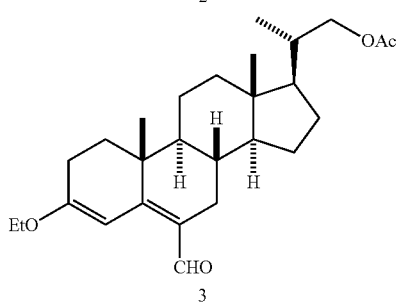
3
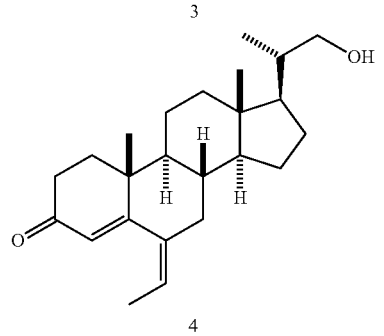
4
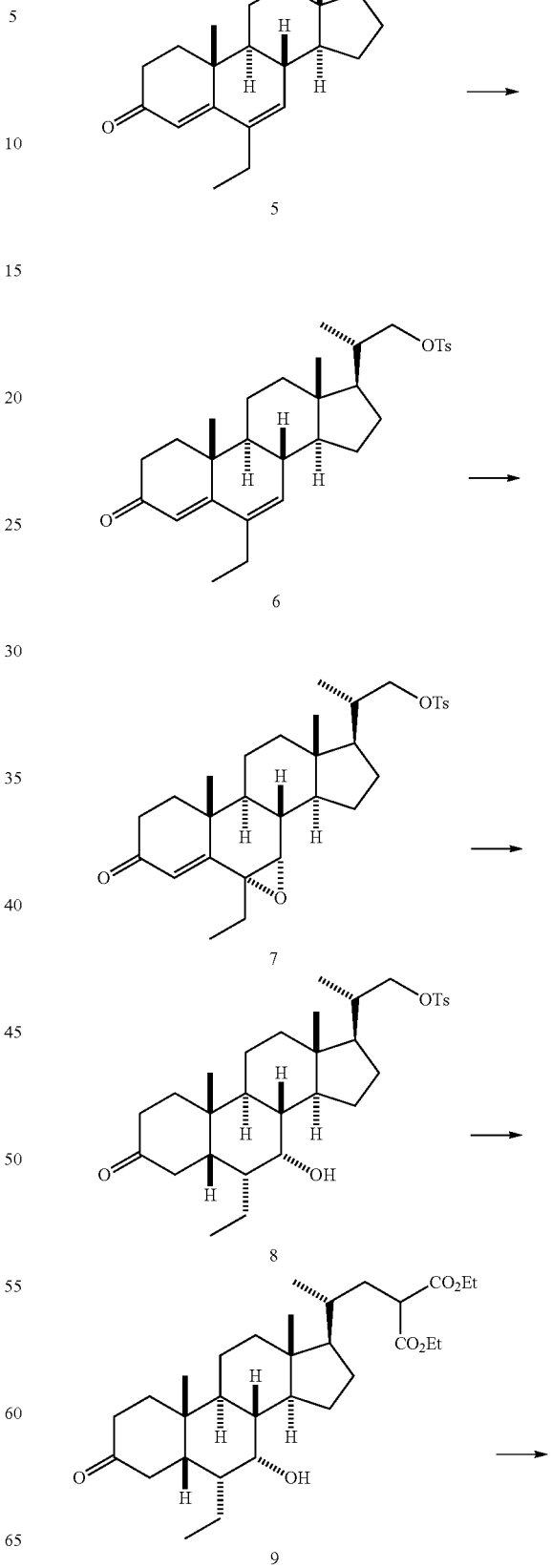

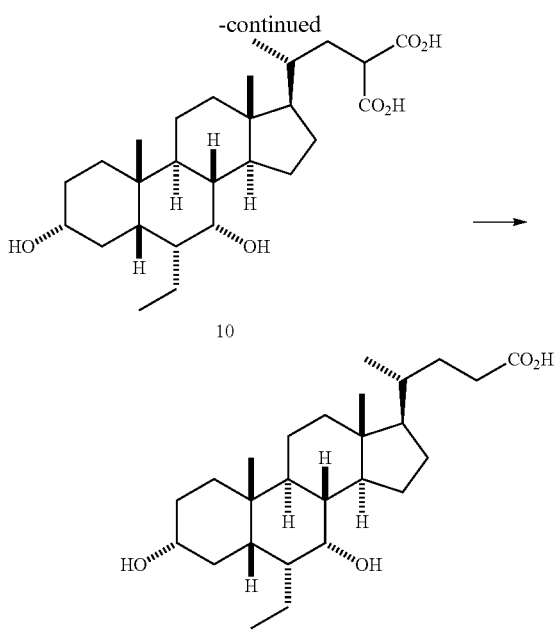

10

Preparation of Compound 1

3-Keto-bisnorcholenol (100 g, 0.302 mol) was added to a solution of 200 ml of DCM, the solution formed was cooled between 0-5° C.; dried $Et_3N$ (280 ml, 2 mol, 6.66 eq) together with a catalytic amount of DMAP (10-13% in weight amount with respect to the steroid) and $Ac_2O$ (66.7 ml, 1 Mol, 3.33 eq) was then added to the reaction mixture and stirred at 5-10° C. for three hours. The resulting reaction mass was treated with 200 ml of a 1 M solution of HCl in water in order to remove the excess $Ac_2O$. The resulting organic phase was washed with at least 4×100 ml of HCl 1M in water to remove $Et_3N$/DMAP that could remain. The final organic phase was concentrated under vacuum and recrystallized with isopropyl alcohol to give 90-93 g of the final product.

$^1$H-RMN: 5.72 (s, 1H, H $C_t$); 4.06 (dd, 10.6 Hz, 3.4 Hz, 1H, $HC_{22}$); 3.76 (dd, 1H, 10.6 Hz, 7.3 Hz, $HC_{22}$); 2.45-2.24 (m, 4H); 2.05 (s, 3H, —$COCH_3$), 2.04-1.99 (m, 2H); 1.87-1.79 (m, 2H); 1.76-1.59 (m, 4H); 1.56-1.30 (m, 4H); 1.18 (s, 3H, $CH_3$); 1.23-1.89 (m, 5H); 1.01 (d, 6.6 Hz, 3H, $H_3O_{21}$); 0.73 (s, 3H, $CH_3$).

Preparation of Compound 2

Anhydrous solvents/reagents and inert atmosphere were used.

Compound 1 (47.54 g, 0.127 mol) was dissolved in 190 ml of THF at room temperature, to this solution was added EtOH (35 ml), p-TSA (1 g, catalytic amount) and triethyl-orthoformate (63.74 ml, 3 eq). The resulting reaction mixture was heated to 40° C. for about 6 h. Once the reaction was finished, the resulting reaction mixture was diluted with 200 ml of AcOEt and it was washed two times with 200 ml of a 2M solution of $K_2OO_3$ in water. The resulting organic solution was then dried before removing the solvent and a solid residue was obtained (yellow solid that was used directly in the following reaction).

$^1$H-RMN: 5.20 (m, 1H, H $C_6$); 5.11 (s, $Ha_4$); 4.06 (dd, 10.6 Hz, 3.4 Hz, 1H, $HC_{22}$); 3.82-3.70 (m, 3, $HC_{22}$, O—$CH_2CH_3$); 2.05 (s, 3H, —$COCH_3$); 2.37-0.93 (m, 19H); 1.30 (t, 3H, —$OCH_2CH_3$); 0.97 (s, 3H, $CH_3$); 1.01 (d, 6.6 Hz, 3H, $H_3O_{21}$); 0.73 (s, 3H, $CH_3$).

Preparation of Compound 3

To a cool suspension (0-5° C.) formed by the residue obtained in the previous example and 250 ml of dry DMF was added at once a previous formed solution of 16.2 ml of $POCl_3$ in 80 ml of DMF (0.173 Mol, 1.05 eq from compound 2). The reaction mixture was stirred overnight and was then treated with 200 ml of a 2M solution of $K_2CO_3$ in water and 200 ml of AcOEt. The organic phase was washed again with 100 ml of a 2 M solution of $K_2CO_3$ and 100 ml of water. The organic solution was dried and evaporated until obtaining a residue that was used directly in the next step.

$^1$H-RMN: 10.25 (s, 1H, COH); 6.29 (s, 1H, $HC_4$); 4.07 (m, 1H, $HC_{22}$), 3.78 (m, 1H, $HC_{22}$); 2.05 (s, 3H, —$COCH_3$); 2.55-0.78 (m, 20H); 1.08 (s, 3H, $CH_3$); 1.02 (d, 6.6 Hz, 3H, $H_3O_{21}$); 0.73 (s, 3H, $CH_3$).

Preparation of Compound 4

Anhydrous solvents/reagents and inert atmosphere were used.

The residue obtained in the previous example was dissolved in 100 ml of THF and cooled to 0-5° C., a 3M solution of MeMgCl (225 ml, 0.765 Mol, 6 eq) was slowly added and the reaction mixture was maintained under stirring for 12 h at rt. The resulting reaction mass was cooled with an ice/water bath and treated with a slow addition of 400 ml of a 2 M solution of HCl in water. The resulting two-phase reaction mixture was kept under stirring for 3 h and then diluted with DCM and neutralized with $NaHCO_3$ until a clean two phase separation was obtained. The organic phase was separated, washed with water and finally dried before evaporating the solvent, 48 g of a solid residue were obtained.

$^1$H-RMN: 5.82 (s, 1H, H $C_4$); 5.66 (m, 1H, —C=CH—$CH_3$); 3.65 (m, 1H, $HC_{22}$); 3.39 (m, 1H, $HC_{22}$); 2.72-2.67 (m, 1H); 2.48-2.30 (m, 2H); 2.08-1.98 (m, 2H); 1.94-1.81 (m, 1H); 1.69 (d, 7 Hz, —C=CH—$CH_3$); 1.77-1.07 (m, 14H); 1.08-1.03 (m, 6H, $CH_3$, $H_3O_{21}$); 0.73 (s, 3H, $CH_3$).

Preparation of Compound 5

A suspension of compound 4 (5.19 g, 14.55 mmol), sodium acetate trihydrate (2.57 g, 18.92 mmol), Pd/C 10% wet (0.655 g) and cyclohexene (118 µL, catalytic amount) in EtOH (85 ml) was prepared and heated to reflux. The reaction was followed by TLC and 4 h later more cyclohexene (118 µL) was added to complete the reaction. Once the reaction was finished, the solvent was evaporated and the residue was extracted with DCM and washed with water. The product was isolated once the solvent was removed. Yield approx. 90%.

$^1$H-RMN: 5.96 (s, 1H, $HC_4$); 5.91 (s, 1H, $HC_7$); 3.65 (m, 1H, $HC_{22}$); 3.39 (m, 1H, $HC_{22}$); 1.24 (t, $CH_2$—$CH_3$); 2.62-0.99 (m, 26H); 0.78 (s, 3H, $CH_3$).

Preparation of Compound 6

Compound 5 (8.29 g, 23.25 mmol) was dissolved in 100 ml of DCM at room temperature, to this solution was added Tosyl chloride (6.67 g, 35 mmol) and $Et_3N$ (4.87 ml, 35 mmol) and the reaction mixture was stirring at room temperature until the starting material was consumed. Once the reaction was finished, the organic phase was washed twice with HCl 1M (100 ml) and once with $NaHCO_3$ (100 ml) and the solvent was evaporated until a residue was obtained. The product was purified by silica gel chromatographic column. Yield 90%.

$^1$H-RMN: 7.81-7.75 (m, 2H, OTs); 7.37-7.31 (m, 2H, OTs); 5.93-5.88 (m, 2H, $HC_4$, $HC_7$); 4-3.93 (m, 1H, $HC_{22}$); 3.83-3.76 (m, 1H, $HC_{22}$); 2.45 (s, 3H, $CH_3$—OTs); 2.62-0.95 (m, 31H); 0.72 (s, 3H, $CH_3$).

Preparation of Compound 7

Compound 6 was added to a solution of metachloroperbenzoic acid (1.8 eq.) and $CHCl_3$ (10 vol) at 0/5° C., and the mixture stirred at this temperature for 16 h. The resulting reaction mass was treated with sodium sulfite 20% (5 vol) and DCM (10 vol). The resulting organic phase was extracted with saturated sodium bicarbonate, aq. NaCl and finally water. The final organic phase was concentrated under vacuum and purified by column chromatography to yield a white solid. UPLC purity: 98.47%.

$^1$H-NMR (500 MHz, CDCl$_3$) δ 7.77 (d, J=8.3 Hz, 2H), 7.39-7.31 (m, 2H), 6.23 (s, 1H), 3.99 (dd, J=9.3, 3.2 Hz, 1H), 3.75 (dd, J=9.3, 6.7 Hz, 1H), 2.99 (d, J=1.0 Hz, 1H), 2.62-2.38 (m, 1H), 2.45 (s, 3H), 2.29 (dd, J=14.0, 7.4 Hz, 1H), 1.95-1.10 (m, 17H), 1.03 (s, 3H), 0.98 (d, J=6.6 Hz, 3H), 0.87 (t, J=7.5 Hz, 3H), 0.70 (s, 3H).

Preparation of Compound 8

Compound 7 was dissolved in a dioxane/EtOH mixture and DMAP (13 eq) and Pd/C (5%) (1 g/g) were then added. The reaction medium was inerted and H$_2$ was charged at atmospheric pressure. The reaction mixture was stirred at 20/25° C. for 25 h. The resulting suspension was filtered over celite and the resulting mother liquors were extracted with DCM and 2M HCl. The resulting organic phase was concentrated in vacuo and the resulting oil was suspended in DMF, Pd/C (10%) was added, and H$_2$ was charged at atmospheric pressure for 12 h. The resulting reaction mixture was concentrated to yield a crude (oil) that was purified by column chromatography (AcOEt:Heptane 1:2) to give a white solid. UPLC purity: 95%.

$^1$H-NMR (400 MHz, CDCl$_3$) δ 7.77 (d, J=8.2 Hz, 2H), 7.33 (d, J=8.2 Hz, 2H), 3.97 (dd, J=9.2, 3.0 Hz, 1H), 3.77 (dd, J=9, 2, 6.9 Hz, 1H), 3.73 (s, 1H), 3.03 (t, J=12 Hz, 1H), 2.43 (s, 3H), 2.40-0.7 (m, 22H), 2.43 (s, 3H), 0.98 (d, J=9.4 Hz, 3H), 0.88 (t, J=7.3 Hz, 3H), 0.65 (s, 3H).

Preparation of Compound 9

NaH was suspended in THF and diethyl malonate was added. The resulting solution was heated to 20/25° C., compound 8 was added and the mixture heated to 60° C. After 18 h, the mixture was extracted with water and EtOAc and the resulting organic phase was concentrated under vacuum to give an oily residue which was not purified. Quantified yield 81%.

$^1$H-NMR (500 MHz, CDCl$_3$) δ 4.59-4.08 (m, 4H), 3.77 (t, J=2.4 Hz, 1H), 3.44 (dd, J=11.1, 3.9 Hz, 1H), 3.06 (dd, J=15.3, 13.4 Hz, 1H), 2.40 (td, J=14.3, 5.1 Hz, 1H), 2.31-2.19 (m, 1H), 2.19-1.89 (m, 6H), 1.74-1.10 (m, 18H), 1.26 (dd, J=14.7, 7.2 Hz, 3H), 0.99 (s, 3H), 0.95 (d, J=6.3 Hz, 3H), 0.89 (t, J=7.4 Hz, 3H), 0.68 (s, 3H).

Preparation of Compound 10

Compound 9 was suspended in water and NaOH (50%) (1.25 vol) was added, the reaction mixture was heated to 90° C. and on the hot reaction a prepared solution of NaBH$_4$ (2.2 eq) in water (2.5 vol) and NaOH (50%)(1.25 vol). The reaction mixture was heated under reflux for two hours. After completion of the reaction, the reaction mixture was cooled to 20/25° C. and a solution of 2N HCl (10 vol) was added, after checking that the pH was acid, AcOEt was added. The resulting organic phase was evaporated under vacuum to yield an oil that was not purified. Quantified yield 67%.

Preparation of Obeticholic Acid

The oil resulting from the previous reaction was suspended in xylene and heated to 120/140° C. After completion of the reaction, the reaction mass was concentrated in vacuo to give an oil that was purified by column chromatography (DCM/MeOH). Yield 88%. Purity by UPLC (90%).

Example 2: Synthesis of α-Ethyl Isomer

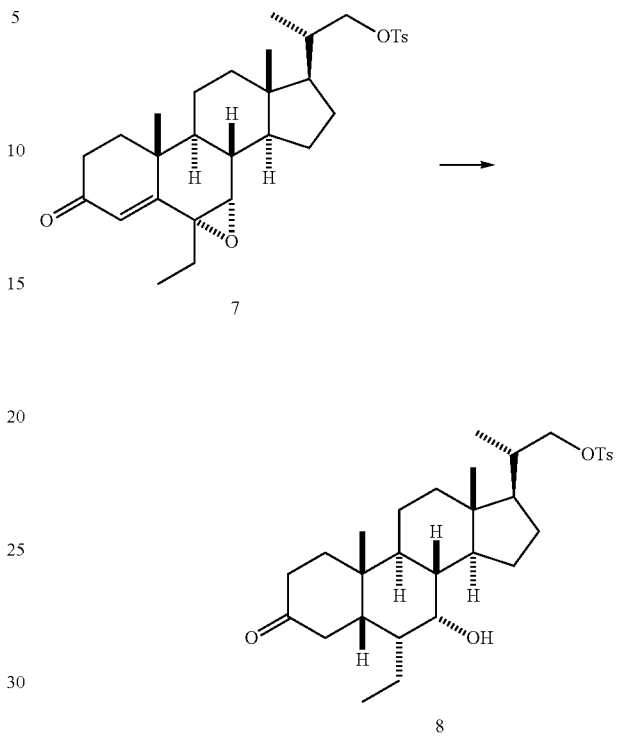

Alternatively, compound 8 was selectively obtained by the following process.

Compound 7 was dissolved in EtOH and then DMAP (9 eq) and Pt/C wet (5%) were added. The reaction medium was inerted and H$_2$ was charged at atmospheric pressure. The reaction mixture was stirred at 40° C. for 21 h. The resulting suspension was filtered over celite and the resulting mother liquors were extracted with DCM and 2M HCl. The resulting organic phase was concentrated in vacuo and the resulting oil was suspended in DMF, Pd/C (5%) was added, and H$_2$ was charged at atmospheric pressure for 12 h. The resulting reaction mixture was concentrated to yield a crude (oil) that was purified by column chromatography (AcOEt: Heptane 1:2) to give a white solid. UPLC purity: 95%

Example 3: Synthesis of β-Ethyl Isomer

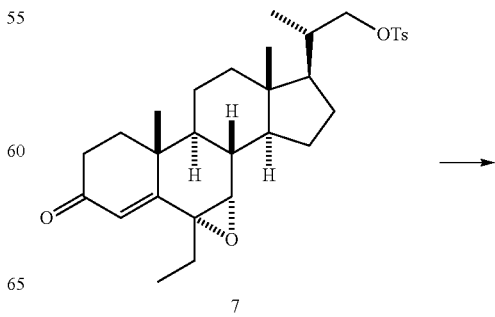

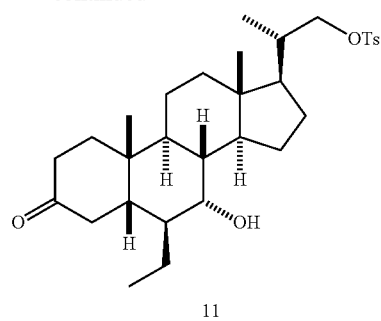

11

Compound 7 was dissolved in DMF, and Pd/CaCO₃ (5%) (4 g/g) was added. The reaction medium was inerted and H₂ was charged at atmospheric pressure. The reaction mixture was stirred at 20/25° C. for 3 h. The resulting suspension was filtered over Celite and the resulting mother liquors were concentrated in vacuo to give an oily residue that was purified by column chromatography (AcOEt:Heptane 1:2) to provide a white solid. UPLC purity: 98%.

¹H-NMR (400 MHz, CDCl₃) δ 7.77 (d, J=8.2 Hz, 2H), 7.33 (d, J=7.9 Hz, 2H), 3.98 (dd, J=8.8, 2.6 Hz, 1H), 3.83-3.75 (m, 2H), 3.66 (s, 1H), 3.37-3.25 (m, 1H), 2.44 (s, 3H), 2.40-0.80 (m, 22H), 1.02 (s, 3H), 0.99 (d, J=6.5 Hz, 3H), 0.91 (t, J=6.7 Hz, 3H), 0.67 (s, 3H).

Alternatively, compound 11 was selectively obtained by the following processes.

Compound 7 was dissolved in acetonitrile, and Pd/BaSO₄ (5%) (1 g/g) was added. The reaction medium was inerted and H₂ was charged at atmospheric pressure. The reaction mixture was stirred at 20/25° C. for 4 h. The resulting suspension was filtered over Celite and the resulting mother liquors were concentrated in vacuo to give an oily residue that was purified by column chromatography (AcOEt:Heptane 1:2) to provide a white solid. UPLC purity: 98%.

Compound 7 was dissolved in acetonitrile, and Pd/Al₂O₃ (5%) (1 g/g) was added. The reaction medium was inerted and H₂ was charged at atmospheric pressure. The reaction mixture was stirred at 20/25° C. for 4 h. The resulting suspension was filtered over Celite and the resulting mother liquors were concentrated in vacuo to give an oily residue that was purified by column chromatography (AcOEt:Heptane 1:2) to provide a white solid. UPLC purity: 98%.

Compound 7 was dissolved in a dioxane/EtOH mixture (1:1), and Pd/C wet (10%) (0.1 g/g) was added. The reaction medium was inerted and H₂ was charged at atmospheric pressure. The reaction mixture was stirred at 40° C. for 21 h. The resulting suspension was filtered over Celite and the resulting mother liquors were concentrated in vacuo to give an oily residue that was purified by column chromatography (AcOEt:Heptane 1:2) to provide a white solid. UPLC purity: 98%.

Formic acid (7 eq) and triethylamine (2.9 eq) were added to a suspension of Pd₂(dba)₃ (0.03 eq) and PPh₃ (0.03 eq) in dioxane. Then, compound 7 in dioxane was added. The reaction mixture was stirred at 80° C. for 3 h. The resulting reaction mixture was concentrated in vacuo to give a crude (oil) that was purified by column chromatography (AcOEt:Heptane 1:2) to provide a white solid. UPLC purity: 95%.

Example 4: Alternative Synthesis of Compound 9

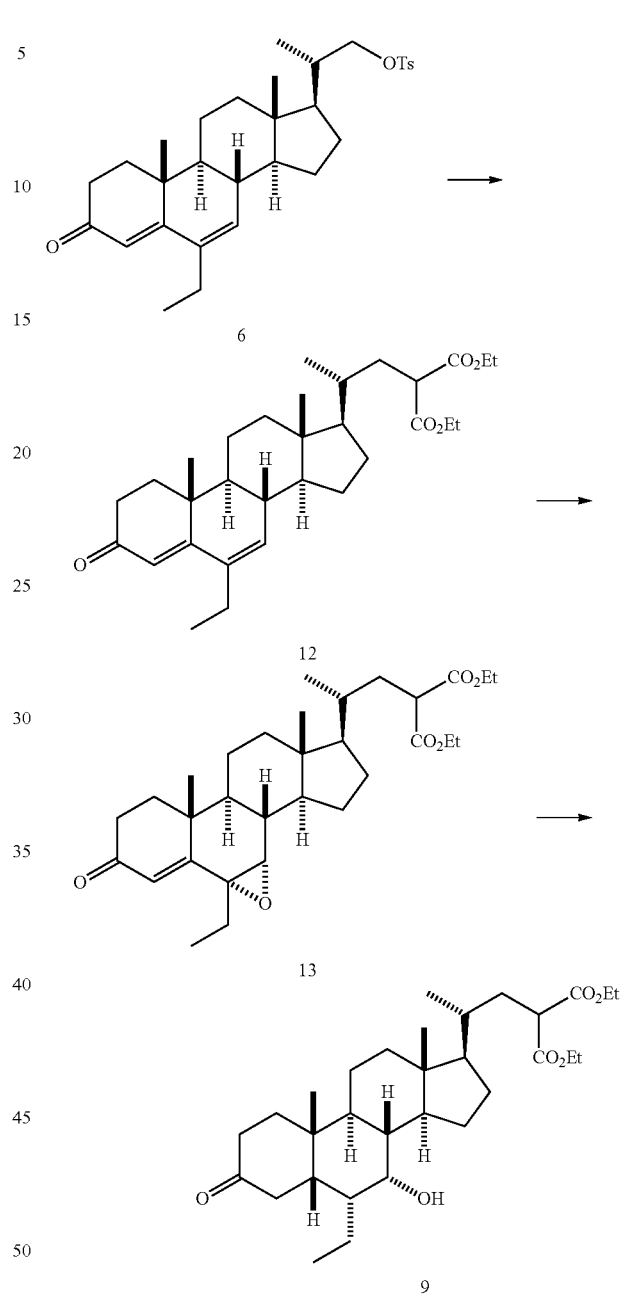

Preparation of Compound 12

Under inert atmosphere, a suspension of 60% NaH (7 eq) in dry THF (10 vol) was prepared, the temperature was lowered to 0/5° C. and diethyl malonate (7 eq.) was added. The reaction mixture was heated to 20/25° C. for 30 minutes, compound 6 was added, and the mixture heated at reflux for 4 hours (follow by TLC). After completion of the reaction water and ethyl acetate were added. The resulting organic phase was distilled in vacuo to give an oil which was purified by column chromatography (EtOAc/heptane). UPLC purity: 98%.

¹H-NMR (400 MHz, CDCl₃) δ 5.94 (s, 1H), 5.88 (s, 1H), 4.25-4.11 (m, 4H), 3.41 (dd, J=11.1, 2.5 Hz, 1H), 2.61-2.47 (m, 1H), 2.39 (dd, J=17.5, 4.6 Hz, 1H), 2.27-0.8 (m, 19H), 1.24 (ddd, J=14.8, 7.4, 1.3 Hz, 6H), 1.04 (s, 3H), 1.00 (dt, J=7.4, 1.2 Hz, 3H), 0.92 (d, J=5.4 Hz, 3H), 0.71 (s, 3H).

Preparation of Compound 13

Compound 12 was dissolved in 20 vol of dichloromethane and metachloroperbenzoic acid (1.8 eq.) was added in portions. After completion of the reaction, the reaction mixture was added to a solution of 5% sodium carbonate (10 vol). The organic phase was dried, filtered and evaporated in vacuo. The crude product was purified by chromatography on silica gel (EtOAc/heptane). Yield: 80% (NMR). Beta epoxide: 5-6%.

$^1$H-NMR (500 MHz, CDCl$_3$) δ 6.23 (s, 1H), 4.37-4.06 (m, 4H), 3.56-3.35 (m, 1H), 3.43 (dd, J=11.1, 3.9 Hz, 1H), 3.10-2.95 (m, 1H), 3.02 (s, 1H), 2.57-2.47 (m, 1H), 2.46-2.38 (m, 1H), 2.30 (dd, J=14.1, 7.3 Hz, 1H), 2.21-2.12 (m, 1H), 2.06-1.96 (m, 2H), 1.92 (ddd, J=13.3, 5.2, 2.2 Hz, 1H), 1.84 (dt, J=16.8, 6.9 Hz, 2H), 1.74-1.58 (m, 4H), 1.54-1.12 (m, 12H), 1.05 (s, 3H), 0.93 (d, J=6.3 Hz, 3H), 0.88 (t, J=7.5 Hz, 3H), 0.73 (s, 3H).

Preparation of Compound 9

Compound 13 was dissolved in dioxane/EtOH mixture and then DMAP (13 eq) and Pd/C (5%) (1 g/g) were added. The reaction medium was inerted and H$_2$ was charged at atmospheric pressure. The reaction mixture was stirred at 20/25° C. for 72 hours. The resulting suspension was filtered over celite and the resulting mother liquors were extracted with DCM and an aqueous solution of 2M HCl (12 vol). The resulting organic phase was concentrated in vacuo and the resulting oil was suspended in DMF, Pd/C (10%) was added and H$_2$ was charged at atmospheric pressure for 12 h. The resulting reaction mixture was concentrated to yield a crude (oil) which was purified by column chromatography (AcOEt:Heptane 1:2) to give a white solid. UPLC purity: 95%.

Example 5: Synthesis of Compound 10 from Compound 8

Preparation of Compound 14

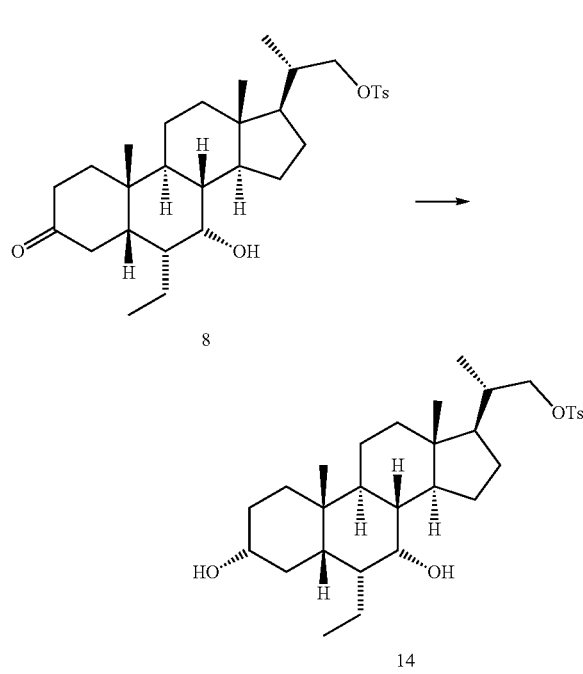

Compound 8 was suspended in THF and (tBuO)$_3$LiAlH (2 mol/mol) was added at 0/5° C., the reaction mixture was kept to this temperature for 2 hours. After completion of the reaction, a solution of 2N HCl (10 vol) was added, once checked the acid pH, AcOEt was added. The resulting organic phase was evaporated under vacuum to yield an oil that was not purified. Quantified yield 100%.

$^1$H-NMR (400 MHz, CDCl$_3$) δ 7.78 (d, J=8.4 Hz, 2H), 7.33 (d, J=8.4 Hz, 2H), 3.99 (dd, J=9.2, 3.2 Hz, 1H), 3.75 (dd, J=9.2, 6.8 Hz, 1H), 3.67 (s, 1H), 3.41-3.38 (m, 1H), 2.44 (s, 3H), 1.91-1.18 (m, 18H), 0.98 (d, J=6.4 Hz, 3H), 0.91-0.87 (m, 7H), 0.62 (s, 3H).

Preparation of Compound 10

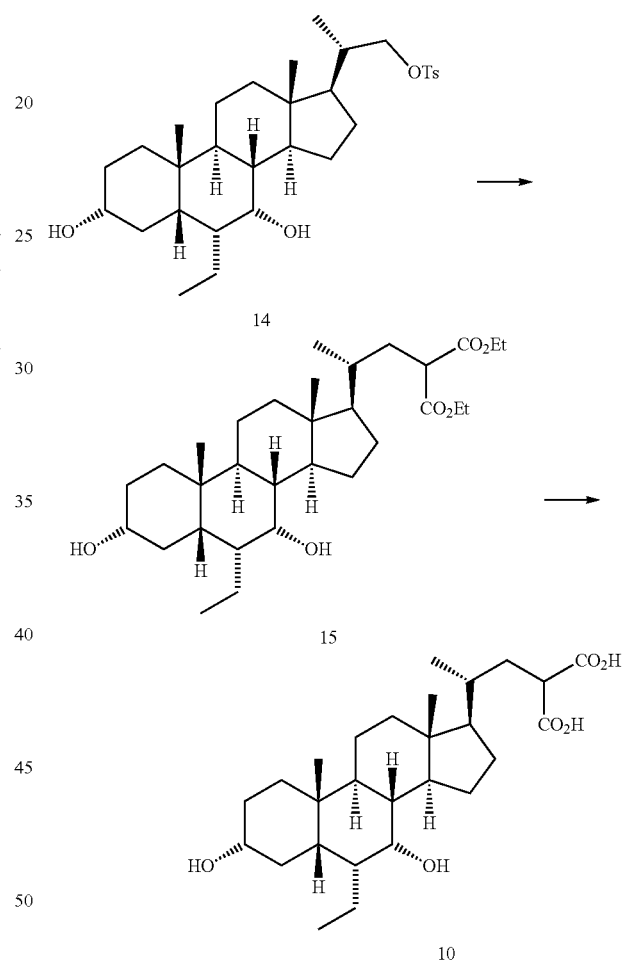

EtONa was suspended in EtOH and diethyl malonate was added. The resulting solution was stirred at 20/25° C., compound 14 was added and the mixture heated to 60° C. After 18 h, a solution of aqueous NaOH (4M) (2 L/Kg) was added and the reaction mixture was heated at 40/50° C. for two hours. After completion of the reaction, ethanol was removed and the reaction mixture was cooled to 20/25° C. A solution of 2N H$_2$SO$_4$ (10 L/Kg) and AcOEt (10 L/Kg) were added. The resulting organic phase was extracted with an aqueous Na$_2$CO$_3$ (10 L/Kg) and then with water (10 L/Kg). The resulting organic phase was concentrated under vacuum to give a solid residue of compound 10 which was not purified. Quantified yield 70%.

$^1$H-NMR (400 MHz, MeOD) δ 3.65 (s, 1H), 3.41-3.38 (m, 1H), 3.31-3.29 (m, 1H), 2.15-2.13 (m, 1H), 2.03-1.20 (m, 23H), 0.98 (d, J=7.2 Hz, 3H), 0.92-0.88 (m, 7H), 0.68 (s, 3H).

What is claimed is:

1. A process for preparing a compound of formula (I) or a salt thereof

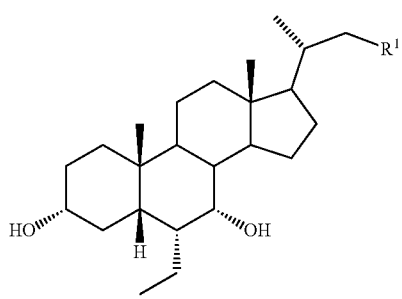

(I)

wherein
R$^1$ is selected from the group consisting of —(CH$_2$)n-OR, —(CH$_2$)n-COOR, —(CH$_2$)nCONR$_2$, —(CH$_2$)n-CH(COOR)$_2$, —(CH$_2$)n-CN, —(CH$_2$)n-halogen, —(CH$_2$)n-OCOR, —(CH$_2$)n-OCOOR, —(CH$_2$)n-OSO$_2$R, —(CH$_2$)n-OSO$_3$R, and —(CH$_2$)n-OSiR$_3$; wherein n is selected from 0, 1, 2, 3 and 4, and each R is independently selected from H, C$_{1-6}$ alkyl, C$_{1-6}$ haloalkyl, C$_{6-10}$ aryl, and (C$_{6-10}$) aryl(C$_{1-6}$)alkyl;

which comprises:

(a) hydrogenation of the double bond and reductive opening of the epoxide of a compound of formula (II) or a salt thereof

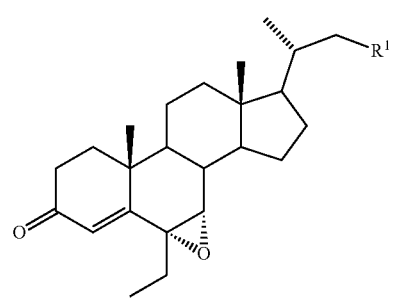

(II)

wherein R$^1$ is as defined above, to obtain a compound of formula (IIIa) and/or a compound of formula (IIIb), or a salt or solvate thereof

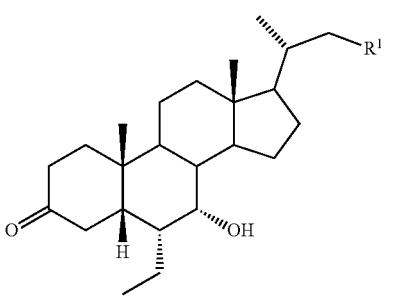

(IIIa)

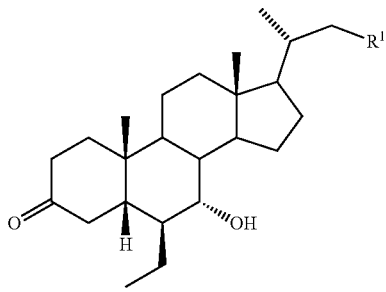

(IIIb)

wherein R$^1$ is as defined above, and (b) conversion of a compound of formula (IIIa) and/or a compound of formula (IIIb), or a salt thereof, into a compound of formula (I), or a salt thereof.

2. Process according to claim 1, which comprises:

(a) hydrogenation of the double bond and reductive opening of the epoxide of a compound of formula (II), or a salt thereof, to obtain a compound of formula (IIIa), or a salt thereof; and (b) reduction of a compound of formula (IIIa), or a salt thereof, to obtain a compound of formula (I), or a salt thereof.

3. Process according to claim 1, which comprises:

(a) hydrogenation of the double bond and reductive opening of the epoxide of a compound of formula (II), or a salt thereof, to obtain a compound of formula (IIIb), or a salt thereof;

(b) conversion of a compound of formula (IIIb), or a salt thereof, into a compound of formula (I), or a salt thereof, by a process comprising:

oxidation of a compound of formula (IIIb), or a salt thereof, to obtain a compound of formula (IV) or a salt thereof

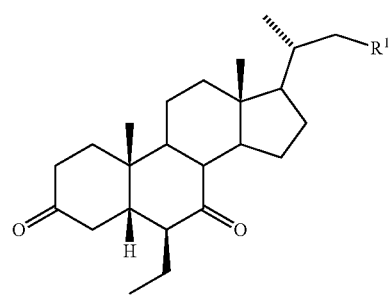

(IV)

wherein R$^1$ is as defined in claim 1, epimerization of a compound of formula (IV), or a salt thereof, to obtain a compound of formula (V) or a salt thereof (V)

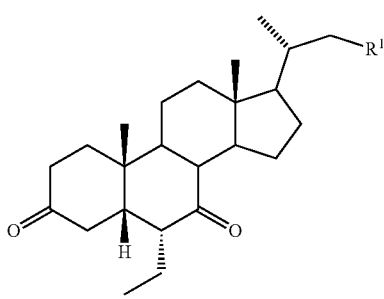

wherein R¹ is as defined in claim 1, and
reduction of a compound of formula (V), or a salt thereof.

4. Process according to claim 1, wherein step (a) is carried out in the presence of Pd/C, Pt/C or $PtO_2$, and a base.

5. Process according to claim 1, wherein step (a) is carried out in the presence of $Pd/CaCO_3$, $Pd/Al_2O_3$, $Pd/BaCO_3$, Pd/C, $Pd_2(dba)_3$ or $Pd(PPh_3)_4$.

6. Process according to claim 1, which further comprises converting R¹ into a different R¹ group after step (a) and/or after step (b).

7. Process according to claim 1, wherein the compound of formula (II), or a salt thereof, is obtained by a process comprising epoxidation of a compound (VI) or a salt thereof (VI)

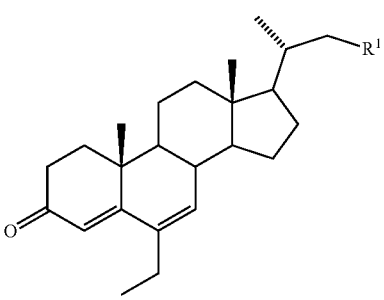

wherein R¹ is as defined in claim 1.

8. Process according to claim 7, wherein the compound of formula (VI), or a salt thereof, is obtained by a process comprising isomerization of a compound (VII) or a salt thereof (VII)

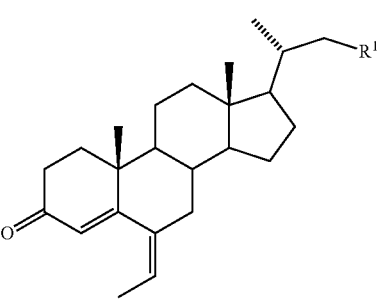

wherein R¹ is selected from the group consisting of —$(CH_2)$n-OR, —$(CH_2)$n-COOR, —$(CH_2)$nCONR$_2$, —$(CH_2)$n-CH(COOR)$_2$, —$(CH_2)$n-CN, —$(CH_2)$n-halogen, —$(CH_2)$n-OCOR, —$(CH_2)$n-OCOOR, —$(CH_2)$n-OSO$_2$R, —$(CH_2)$n-OSO$_3$R, and —$(CH_2)$n-OSiR$_3$;
wherein n is selected from 0, 1, 2, 3 and 4, and each R is independently selected from H, $C_{1-6}$ alkyl, $C_{1-6}$ haloalkyl, $C_{6-10}$ aryl, and $(C_{6-10})$aryl$(C_{1-6})$alkyl.

9. Process according to claim 8, wherein the compound of formula (VII), or a salt or solvate thereof, is obtained by a process comprising:
converting a compound of formula (X) or a salt or solvate thereof (X)

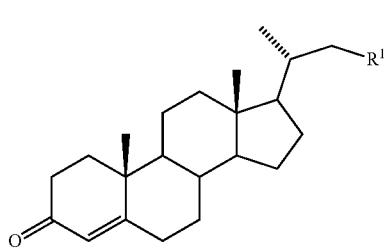

wherein R¹ is selected from the group consisting of —$(CH_2)$n-OR, —$(CH_2)$n-COOR, —$(CH_2)$nCONR$_2$, —$(CH_2)$n-CH(COOR)$_2$, —$(CH_2)$n-CN, —$(CH_2)$n-halogen, —$(CH_2)$n-OCOR, —$(CH_2)$n-OCOOR, —$(CH_2)$n-OSO$_2$R, —$(CH_2)$n-OSO$_3$R, and —$(CH_2)$n-OSiR$_3$; wherein n is selected from 0, 1, 2, 3 and 4, and each R is independently selected from H, $C_{1-6}$ alkyl, $C_{1-6}$ haloalkyl, $C_{6-10}$ aryl, and $(C_{6-10})$aryl$(C_{1-6})$alkyl into an enol ether of formula (IX) or a salt thereof (IX)

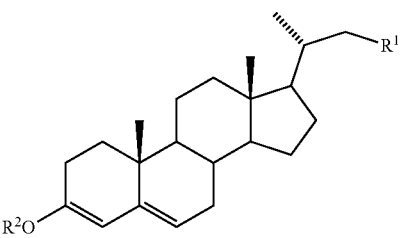

wherein R¹ is selected from the group consisting of —$(CH_2)$n-OR, —$(CH_2)$n-COOR, —$(CH_2)$nCONR$_2$, —$(CH_2)$n-CH(COOR)$_2$, —$(CH_2)$n-CN, —$(CH_2)$n-halogen, —$(CH_2)$n-OCOR, —$(CH_2)$n-OCOOR, —$(CH_2)$n-OSO$_2$R, —$(CH_2)$n-OSO$_3$R, and —$(CH_2)$n-OSiR$_3$;
wherein n is selected from 0, 1, 2, 3 and 4, and each R is independently selected from H, $C_{1-6}$ alkyl, $C_{1-6}$ haloalkyl, $C_{6-10}$ aryl, and $(C_{6-10})$aryl$(C_{1-6})$alkyl;
and R² is selected from $C_{1-6}$ alkyl, $C_{6-10}$ aryl, $(C_{6-10})$aryl $(C_{1-6})$alkyl and SiR'$_3$, wherein each R' is independently selected from $C_{1-6}$ alkyl, $C_{6-10}$ aryl and $C_{1-6}$ alkoxy,
converting a compound of formula (IX), or a salt thereof, into a compound of formula (VII), or a salt thereof.

10. Process according to claim 9, wherein the compound of formula (IX), or a salt thereof, is converted into a compound of formula (VII), or a salt thereof, by a process comprising either:
(A) formylation of a compound of formula (IX), or a salt thereof, to provide a compound of formula (VIII) or a salt thereof

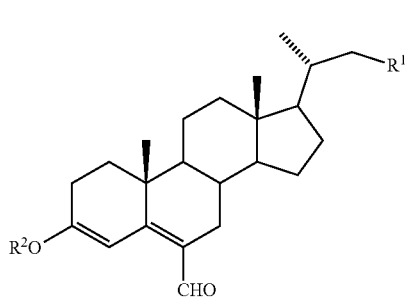

(VIII)

wherein $R^1$ and $R^2$ are as defined in claim 9, and methylation followed by dehydration of a compound of formula (VIII), or a salt thereof, to provide a compound of formula (VII), or a salt thereof; or (B) Mannich reaction of a compound of formula (IX), or a salt thereof, followed by elimination of the resulting amine to provide a compound of formula (VII), or a salt thereof.

11. Process according to claim 1, wherein the compound of formula (I) is selected from obeticholic acid, INT-767 and ECDCOH, or a salt thereof

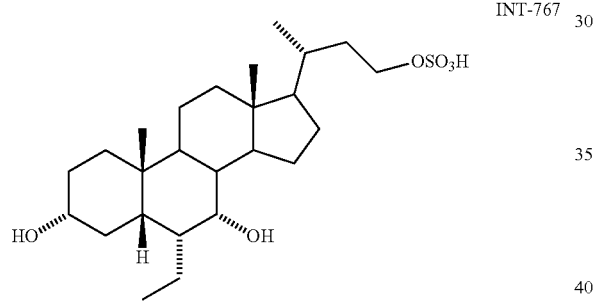

INT-767

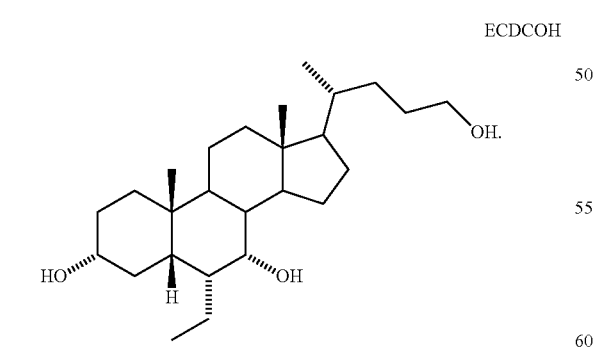

ECDCOH

12. Process according to claim 1, for the preparation of obeticholic acid, or a salt thereof, which comprises:

(a) hydrogenation of the double bond and reductive opening of the epoxide of a compound of formula (II') or a salt thereof

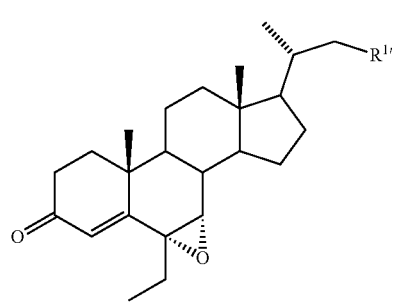

(II')

wherein $R^h$, is selected from the group consisting of —OH, halogen, —OCOR, —OSO$_2$R, —CH(COOH)$_2$, —CH(COOR)$_2$, —CH$_2$—COOH and —CH$_2$—COOR; wherein each R is independently selected from $C_{1-6}$ alkyl, $C_{1-6}$ haloalkyl, $C_{6-10}$ aryl, and $(C_{6-10})$aryl$(C_{1-6})$alkyl, to obtain a compound of formula (IIIa') or a salt thereof

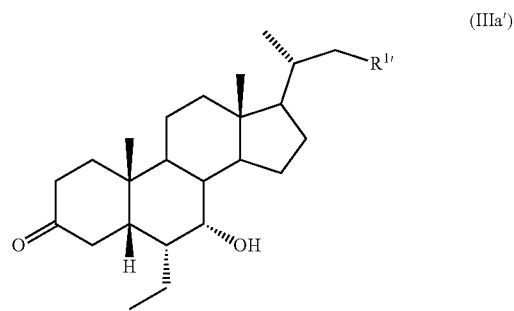

(IIIa')

wherein $R^{1\prime}$ is as defined above, and (b) conversion of a compound of formula (IIIa'), or a salt thereof, into obeticholic acid, or a salt thereof, by a process comprising either:

(A) if $R^{1\prime}$, in the compound of formula (IIIa'), or a salt or solvate thereof, is —CH$_2$—COOH or —CH$_2$—COOR, wherein R is selected from $C_{1-6}$ alkyl, $C_{1-6}$ haloalkyl, $C_{6-10}$ aryl, and $(C_{6-10})$aryl$(C_{1-6})$alkyl:

hydrolysis of the ester groups if $R^{1\prime}$ is —CH$_2$—COOR, to obtain a compound wherein $R^{1\prime}$ is —CH$_2$—COOH, and reduction of the ketone group, wherein the reduction of the keto group can be performed before hydrolysis of the ester group, or after hydrolysis of the ester group; or (B) if $R^{1\prime}$ in the compound of formula (IIIa'), or a salt thereof, is —CH(COOH)$_2$ or —CH(COOR)$_2$, wherein R is selected from $C_{1-6}$ alkyl, $C_{1-6}$ haloalkyl, $C_{6-10}$ aryl, and $(C_{6-10})$aryl$(C_{1-6})$alkyl:

hydrolysis of the ester groups if $R^{1\prime}$ is —CH(COOR)$_2$, to obtain a compound wherein $R^{1\prime}$ is —CH(COOH)$_2$, decarboxylation reaction, and reduction of the ketone group, wherein the reduction of the keto group can be performed before hydrolysis of the ester groups, or before decarboxylation reaction, or after decarboxylation reaction; or (C) if $R^{1\prime}$ in the compound of formula (IIIa'), or a salt thereof, is selected from —OH, halogen, —OCOR, and —OSO$_2$R, wherein R is selected from $C_{1-6}$ alkyl, $C_{1-6}$ haloalkyl, $C_{6-10}$ aryl, and $(C_{6-10})$aryl$(C_{1-6})$alkyl:

if R¹' is —OH, conversion into a compound wherein R¹' is selected from halogen, —OCOR, and —OSO₂R, wherein R is selected from C₁₋₆ alkyl, C₁₋₆ haloalkyl, C₆₋₁₀ aryl, and (C₆₋₁₀)aryl(C₁₋₆)alkyl,
reaction with a compound of formula CH₂(COOR)₂ wherein each R is independently selected from C₁₋₆ alkyl, C₁₋₆ haloalkyl, C₆₋₁₀ aryl and (C₆₋₁₀)aryl(C₁₋₆)alkyl, to obtain a compound wherein R¹' is —CH(COOR)₂,
hydrolysis of the ester groups,
decarboxylation reaction, and
reduction of the ketone group,
wherein the reduction of the keto group can be performed before conversion of —OH into halogen, —OCOR, or —OSO₂R, or before reaction with a compound of formula CH₂(COOR)₂, or before hydrolysis of the ester groups, or before decarboxylation reaction, or after decarboxylation reaction.

13. Process according to claim 1, for the preparation of obeticholic acid, or a salt thereof, which comprises:
(a) hydrogenating the double bond and reductive opening of the epoxide of a compound of formula (II') or a salt thereof

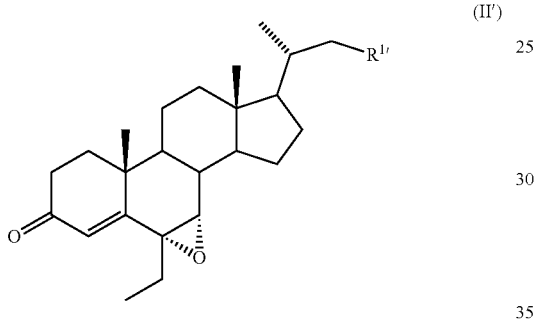

wherein is selected from the group consisting of —OH, halogen, —OCOR and —OSO₂R, wherein each R is independently selected from C₁₋₆ alkyl, C₁₋₆ haloalkyl, C₆₋₁₀ aryl, and (C₆₋₁₀)aryl(C₁₋₆)alkyl,
to obtain a compound of formula (IIIa') or a salt thereof

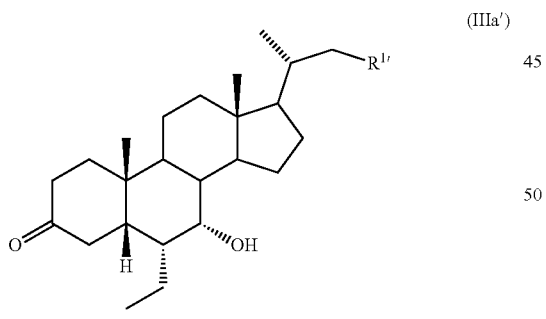

wherein R¹' is as defined above, and
(b) converting a compound of formula (IIIa'), or a salt thereof, into obeticholic acid, or a salt thereof, by a process comprising:
reduction of the ketone group,
reaction with a compound of formula CH₂(COOR)₂ wherein each R is independently selected from C₁₋₆ alkyl, C₁₋₆ haloalkyl, C₆₋₁₀ aryl and (C₆₋₁₀) aryl(C₁₋₆)alkyl, to obtain a compound wherein R¹' is —CH(COOR)₂,
hydrolysis of the ester groups, and
decarboxylation reaction.

14. A compound of formula (II) or a salt thereof

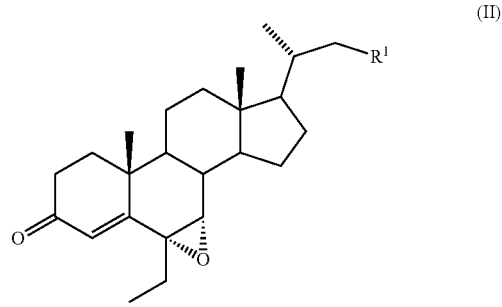

wherein
R¹ is selected from the group consisting of —(CH₂)n-OR, —(CH₂)n-COOR, —(CH₂)n-CONR₂, —(CH₂)n-CH(COOR)₂, —(CH₂)n-CN, —(CH₂)n-halogen, —(CH₂)n-OCOR, —(CH₂)n-OCOOR, —(CH₂)n-OSO₂R, —(CH₂)n-OSO₃R, and —(CH₂)n-OSiR₃; wherein n is selected from 0, 1, 2, 3 and 4, and each R is independently selected from H, C₁₋₆ alkyl, C₁₋₆ haloalkyl, C₆₋₁₀ aryl, and (C₆₋₁₀)aryl(C₁₋₆)alkyl.

15. A compound of formula (IIIa), (VI) or (VII) or a salt thereof

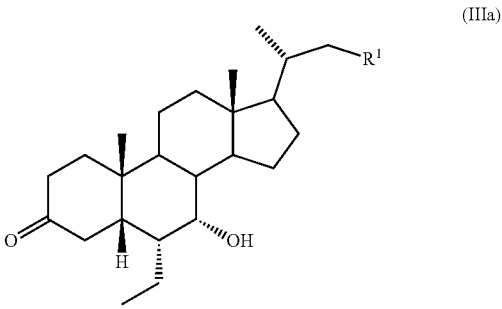

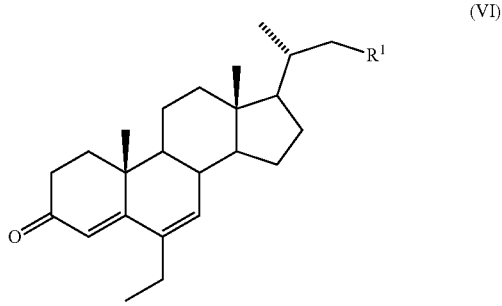

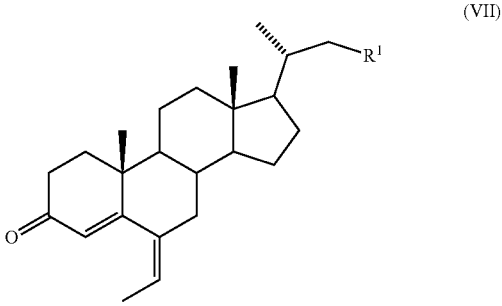

wherein
R¹ is selected from the group consisting of —(CH₂)n-OR, —(CH₂)n-COOR, —(CH₂)n-CONR₂, —(CH₂)n-CH(COOR)₂, —(CH₂)n-CN, —(CH₂)n-halogen, —(CH₂)n-OCOR, —(CH₂)n-OCOOR, —(CH₂)n-OSO₂R, —(CH₂)n-OSO₃R, and —(CH₂)n-OSiR₃; wherein n is selected from 0, 1, 2, 3 and 4, and each R is independently selected from H, C₁₋₆ alkyl, C₁₋₆ haloalkyl, C₆₋₁₀ aryl, and (C₆₋₁₀)aryl(C₁₋₆)alkyl;
provided that R¹ is not —COOH and —CH₂—COOMe in the compound of formula (IIIa).

16. A compound according to claim 14, which is:

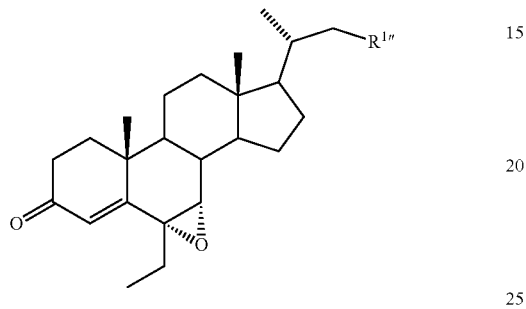

wherein
R¹" is selected from the group consisting of —OH, halogen, -OTs, -OTf, -OMs, —OAc, —CH(COOR)₂ and —CH₂—COOR; wherein each R is independently selected from H and C₁₋₆ alkyl,
or a salt thereof.

17. A compound according to claim 15, selected from the group consisting of:

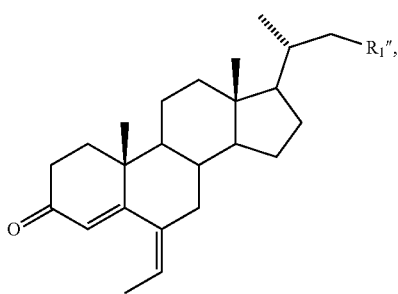

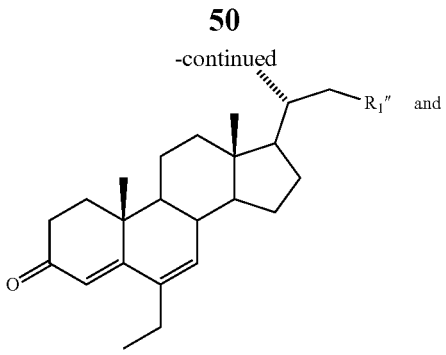

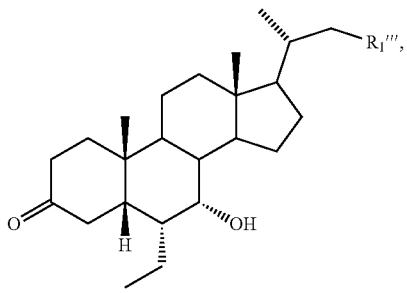

wherein
R¹" is selected from the group consisting of —OH, halogen, -OTs, -OTf, -OMs, —OAc, —CH(COOR)₂ and —CH₂—COOR; wherein each R is independently selected from H and C₁₋₆ alkyl, and R¹'" is selected from the group consisting of —OH, halogen, -OTs, -OTf, -OMs, —OAc, —CH(COOR)₂ and —CH₂—COOR'; wherein each R is independently selected from H and C₁₋₆ alkyl, and R' is selected from H and C₂₋₆ alkyl, or a salt thereof.

18. Process according to claim 4, wherein the base is a pyridine-type base.

* * * * *

UNITED STATES PATENT AND TRADEMARK OFFICE
CERTIFICATE OF CORRECTION

PATENT NO. : 11,104,702 B2
APPLICATION NO. : 16/632304
DATED : August 31, 2021
INVENTOR(S) : Ignacio Herraiz Sierra It is certified that error appears in the above-identified patent and that said Letters Patent is hereby corrected as shown below:

In the Specification

In Column 7, Line 67, delete "material" and insert --material.--.

In Column 9, Line 58 (Approx.), delete "FIG. 1." and insert --The figure--.

In Column 10, Line 17, delete "phenyl" and insert --phenyl.--.

In Column 10, Line 67, delete "dialkylenethanolamine," and insert --dialkylethanolamine,--.

In Column 11, Line 44, delete "$O_{1-6}$" and insert --$C_{1-6}$--.

In Column 11, Line 44, delete "$O_{1-6}$" and insert --$C_{1-6}$--.

In Column 14, Line 48, delete "$5^{th}$ed.," and insert --$5^{th}$ ed.,--.

In Column 21, Line 51 (Approx.), delete "(IIIa)" and insert --(IIIa')--.

In Column 22, Line 2, delete "(IIIa)," and insert --(IIIa'),--.

In Column 22, Line 6 (Approx.), delete "(IIIa)," and insert --(IIIa'),--.

In Column 22, Line 19 (Approx.), delete "(IIIa)," and insert --(IIIa'),--.

In Column 22, Line 34 (Approx.), delete "(IIIa)," and insert --(IIIa'),--.

In Column 22, Line 46, delete "$(O_{6-10})$ aryl" and insert --$(C_{6-10})$aryl--.

In Column 23, Line 20 (Approx.), delete "(IIIa)" and insert --(IIIa')--.

Signed and Sealed this
Twenty-seventh Day of December, 2022

Katherine Kelly Vidal
*Director of the United States Patent and Trademark Office*

CERTIFICATE OF CORRECTION (continued)
U.S. Pat. No. 11,104,702 B2

In Column 23, Line 38, delete "(IIIa)," and insert --(IIIa'),--.

In Column 24, Line 59 (Approx.), delete "($C_{6-10}$) aryl" and insert --($C_{6-10}$)aryl--.

In Column 33, Line 42 (Approx.), delete "RMN:" and insert --NMR:--.

In Column 33, Line 42 (Approx.), delete "$C_t$" and insert --$C_4$--.

In Column 33, Line 46, delete "$H_3O_{21}$" and insert --$H_3C_{21}$--.

In Column 33, Line 63 (Approx.), delete "RMN:" and insert --NMR:--.

In Column 33, Line 63 (Approx.), delete "$Ha_4$" and insert --$HC_4$--.

In Column 33, Line 67, delete "$H_3O_{21}$" and insert --$H_3C_{21}$--.

In Column 34, Line 11 (Approx.), delete "RMN:" and insert --NMR:--.

In Column 34, Line 14 (Approx.), delete "$H_3O_{21}$" and insert --$H_3C_{21}$--.

In Column 34, Line 31, delete "RMN:" and insert --NMR:--.

In Column 34, Line 35, delete "$H_3O_{21}$" and insert --$H_3C_{21}$--.

In Column 34, Line 47, delete "RMN:" and insert --NMR:--.

In Column 34, Line 61, delete "RMN:" and insert --NMR:--.

In Column 36, Line 49 (Approx.), delete "95%" and insert --95%.--.

In the Claims

In Column 41, Claim 1, Line 25 (Approx.), delete "n$CONR_2$" and insert --n-$CONR_2$--.

In Column 41, Claim 1, Line 31 (Approx.), delete "($C_{6-10}$) aryl" and insert --($C_{6-10}$)aryl--.

In Column 41, Claim 1, Line 51 (Approx.), delete "(Ma)" and insert --(IIIa)--.

In Column 41, Claim 1, Line 52 (Approx.), after "salt" delete "or solvate".

In Column 42, Claim 1, Line 16 (Approx.), delete "(Ma)" and insert --(IIIa)--.

In Column 42, Claim 2, Line 24 (Approx.), delete "(Ma)," and insert --(IIIa),--.

In Column 42, Claim 2, Line 26 (Approx.), delete "(Ma)," and insert --(IIIa),--.

CERTIFICATE OF CORRECTION (continued)
U.S. Pat. No. 11,104,702 B2

In Column 42, Claim 3, Line 35, delete "(Mb)," and insert --(IIIb),--.

In Column 43, Claim 8, Line 66, delete "nCONR$_2$" and insert --n-CONR$_2$--.

In Column 44, Claim 9, Line 8 (Approx.), after "salt" delete "or solvate".

In Column 44, Claim 9, Line 10 (Approx.), after "salt" delete "or solvate".

In Column 44, Claim 9, Line 26, delete "nCONR$_2$" and insert --n-CONR$_2$--.

In Column 44, Claim 9, Line 48, delete "nCONR$_2$" and insert --n-CONR$_2$--.

In Column 46, Claim 12, Line 15, delete "R$^h$," and insert --R$^{1'}$,--.

In Column 46, Claim 12, Lines 41-42, after "salt" delete "or solvate".

In Column 47, Claim 13, Line 36 (Approx.), after "wherein" insert --R$^{1'}$--.

In Column 47, Claim 13, Line 63, delete "(C$_{6-10}$) aryl" and insert --(C$_{6-10}$)aryl--.

In Column 49, Claim 17, Lines 35-45 (Approx.), delete " 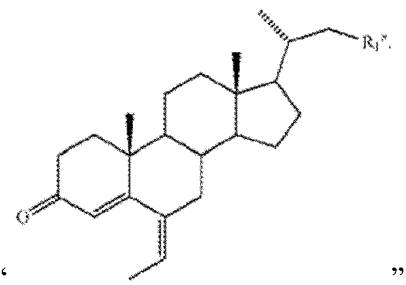 "

and insert -- 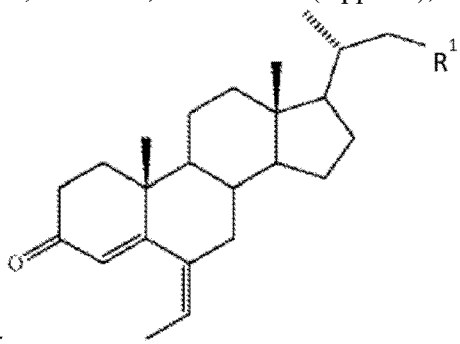 --.

In Column 50, Claim 17, Lines 1-13 (Approx.), delete " 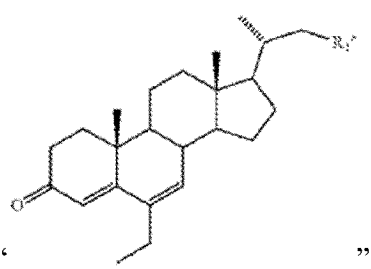 "

CERTIFICATE OF CORRECTION (continued)
U.S. Pat. No. 11,104,702 B2

Page 4 of 4 and insert -- 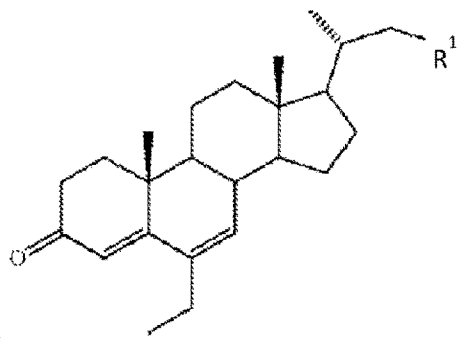 --.

In Column 50, Claim 17, Lines 20-33 (Approx.), delete " 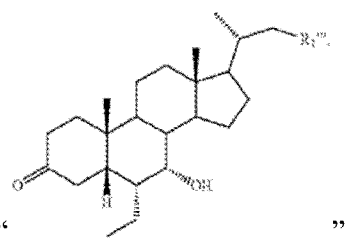 "

and insert -- 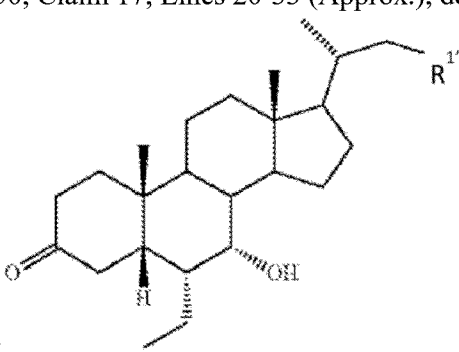 --.

In Column 50, Claim 17, Line 44, delete "Hand" and insert --H and--.